United States Patent
Madan et al.

(10) Patent No.: US 8,147,508 B2
(45) Date of Patent: Apr. 3, 2012

(54) MEDICAL ULTRASOUND SYSTEM AND HANDPIECE AND METHODS FOR MAKING AND TUNING

(75) Inventors: Ashvani K. Madan, Mason, OH (US); Michael R. Lamping, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1144 days.

(21) Appl. No.: 11/784,724

(22) Filed: Apr. 9, 2007

(65) Prior Publication Data

US 2007/0232927 A1    Oct. 4, 2007

Related U.S. Application Data

(62) Division of application No. 11/545,784, filed on Oct. 10, 2006.

(60) Provisional application No. 60/726,625, filed on Oct. 14, 2005.

(51) Int. Cl.
*A61B 17/32* (2006.01)

(52) U.S. Cl. ........................ 606/169; 606/170

(58) Field of Classification Search ............ 606/169, 606/170, 171, 1; 604/22; 601/2; 310/33, 310/316.01, 321, 334, 323.06, 317, 318, 310/320; 600/459, 437

See application file for complete search history.

(56) References Cited

U.S. PATENT DOCUMENTS

| | | | |
|---|---|---|---|
| 3,368,085 A | 2/1968 | McMaster et al. | |
| 3,636,943 A | 1/1972 | Balamuth | |
| 4,783,997 A | 11/1988 | Lynnworth | |
| 5,059,210 A | 10/1991 | Clark et al. | |
| 5,112,300 A | 5/1992 | Ureche | |
| 5,322,055 A | 6/1994 | Davison et al. | |
| 5,397,293 A * | 3/1995 | Alliger et al. | 601/2 |
| 5,630,420 A * | 5/1997 | Vaitekunas | 600/459 |
| 5,688,235 A | 11/1997 | Sakurai et al. | |

(Continued)

FOREIGN PATENT DOCUMENTS

GB    868784    8/1957

(Continued)

OTHER PUBLICATIONS

International Search Report issued regarding International Application No. PCT/US06/40259 (Jan. 11, 2008).

(Continued)

*Primary Examiner* — Ryan Severson
*Assistant Examiner* — Tin Nguyen
(74) *Attorney, Agent, or Firm* — Thompson Hine LLP

(57) ABSTRACT

Several embodiments of medical ultrasound handpieces are described each including a medical ultrasound transducer assembly. An embodiment of a medical ultrasound system is described, wherein the medical ultrasound system includes a medical ultrasound handpiece having a medical ultrasound transducer assembly and includes an ultrasonically-vibratable medical-treatment instrument which is attachable to a distal end of the transducer assembly. An embodiment of a medical ultrasound system is described, wherein the medical ultrasound system has a handpiece including a medical ultrasound transducer assembly and including a housing or housing component surrounding the transducer assembly. A method for tuning a medical ultrasound handpiece includes machining at least a distal non-threaded portion of an instrument-attachment stud of the transducer assembly to match a measured fundamental frequency to a desired fundamental frequency to within a predetermined limit. A method for making a medical ultrasound transducer assembly determines acceptable gains for gain stages of the transducer assembly.

19 Claims, 23 Drawing Sheets

U.S. PATENT DOCUMENTS

| | | | |
|---|---|---|---|
| 5,746,756 A | 5/1998 | Bromfield et al. | |
| 5,776,155 A * | 7/1998 | Beaupre et al. | 606/169 |
| 5,873,873 A | 2/1999 | Smith et al. | |
| 5,938,633 A | 8/1999 | Beaupre | |
| 5,944,737 A * | 8/1999 | Tsonton et al. | 606/205 |
| 6,063,098 A | 5/2000 | Houser et al. | |
| 6,278,218 B1 * | 8/2001 | Madan et al. | 310/312 |
| 6,325,811 B1 | 12/2001 | Messerly | |
| 6,425,907 B1 | 7/2002 | Shibata et al. | |
| 6,491,708 B2 | 12/2002 | Madan et al. | |
| 6,623,500 B1 | 9/2003 | Cook et al. | |
| 6,660,017 B2 | 12/2003 | Beaupre | |
| 6,719,776 B2 | 4/2004 | Baxter et al. | |
| 2002/0002378 A1 | 1/2002 | Messerly | |
| 2002/0049464 A1 * | 4/2002 | Donofrio et al. | 606/169 |
| 2002/0057541 A1 | 5/2002 | Donofrio | |
| 2002/0091404 A1 | 7/2002 | Beaupre | |
| 2002/0156493 A1 | 10/2002 | Houser et al. | |
| 2002/0183774 A1 | 12/2002 | Witt et al. | |
| 2003/0216766 A1 | 11/2003 | Wiener et al. | |
| 2004/0006269 A1 * | 1/2004 | Novak et al. | 600/437 |
| 2004/0124745 A1 | 7/2004 | Goodson | |
| 2004/0127926 A1 | 7/2004 | Beaupre | |
| 2004/0147947 A1 * | 7/2004 | Donofrio | 606/169 |
| 2004/0193199 A1 | 9/2004 | Hashiguchi | |
| 2004/0230214 A1 | 11/2004 | Donofrio et al. | |
| 2005/0234484 A1 | 10/2005 | Houser et al. | |
| 2007/0106158 A1 | 5/2007 | Madan et al. | |
| 2007/0191713 A1 | 8/2007 | Eichmann et al. | |
| 2007/0232920 A1 | 10/2007 | Kowalski et al. | |
| 2007/0232926 A1 | 10/2007 | Stulen et al. | |
| 2007/0232928 A1 | 10/2007 | Wiener et al. | |
| 2007/0239025 A1 | 10/2007 | Wiener et al. | |

FOREIGN PATENT DOCUMENTS

| | | |
|---|---|---|
| WO | 00/62688 | 10/2000 |

OTHER PUBLICATIONS

International Search Report, PCT/US2008/079295 (Feb. 24, 2009).
Office Action, U.S. Appl. No. 11/548,407 (Oct. 29, 2008).
International Preliminary Report on Patentability, PCT/US2006/040259 (Apr. 2, 2009).
PCT, International Search Report, PCT/US06/39904 (Jun. 18, 2008).
Office Action, U.S. Appl. No. 11/548,407 (Aug. 7, 2009) (13 pages).
CN, Notification of First Office Action, Chinese Application No. 200680042713.8 (May 12, 2010).
US, Office Action, U.S. Appl. No. 11/784,715 (Apr. 14, 2010).
US, Office Action, U.S. Appl. No. 11/784,725 (Feb. 17, 2010).
US, Office Action, U.S. Appl. No. 11/784,725 (Aug. 4, 2010).
CN, First Office Action, Chinese Application No. 200680042602.7, (Jul. 2, 2010).
PCT, International Preliminary Report on Patentability, International Application No. PCT/US2008/079295, (Apr. 13, 2010).
US, Office Action, U.S. Appl. No. 11/545,784, (Oct. 6, 2010).
US, Office Action, U.S. Appl. No. 11/545,784, (Apr. 12, 2011).
US, Office Action, U.S. Appl. No. 11/548,407, (Oct. 29, 2010).
US, Office Action, U.S. Appl. No. 11/784,725, (Nov. 10, 2010).
US, Advisory Action, U.S. Appl. No. 11/784,725, (Apr. 28, 2011).
US, Office Action, U.S. Appl. No. 11/784,714 (Sep. 15, 2011).
US, Office Action, U.S. Appl. No. 11/784,726 (Aug. 12, 2011).

* cited by examiner

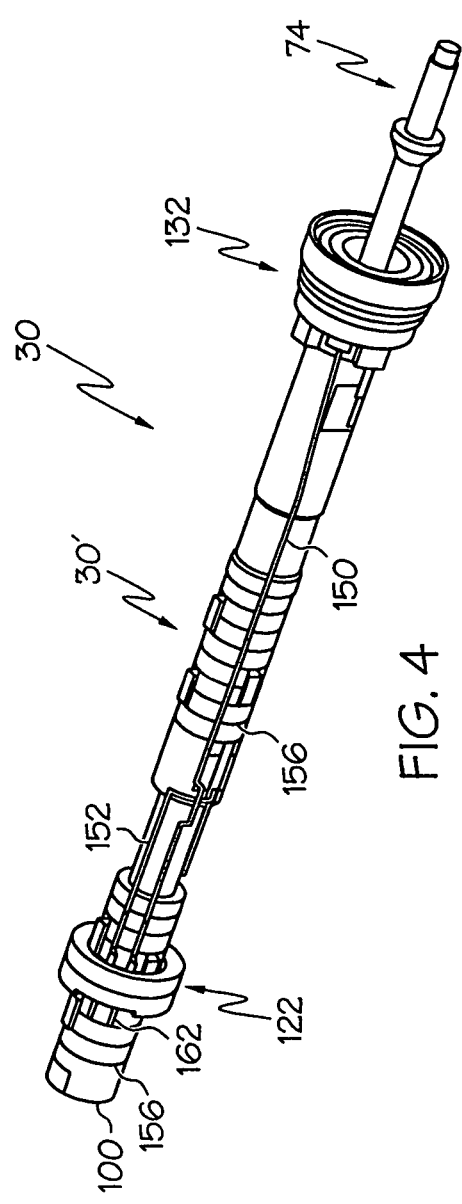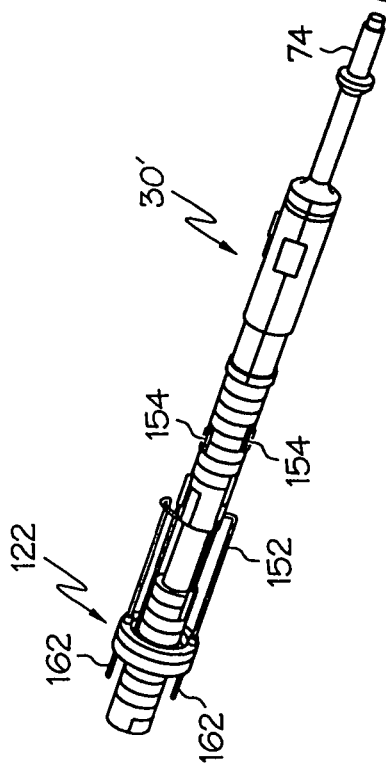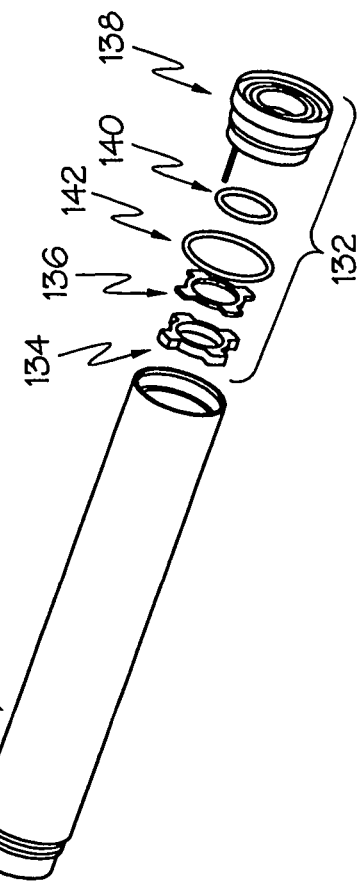

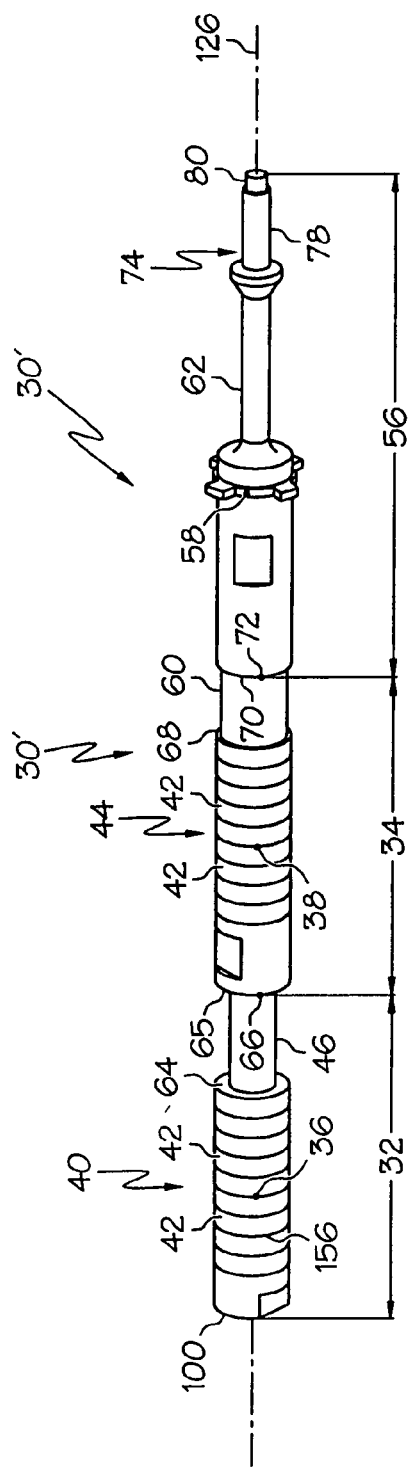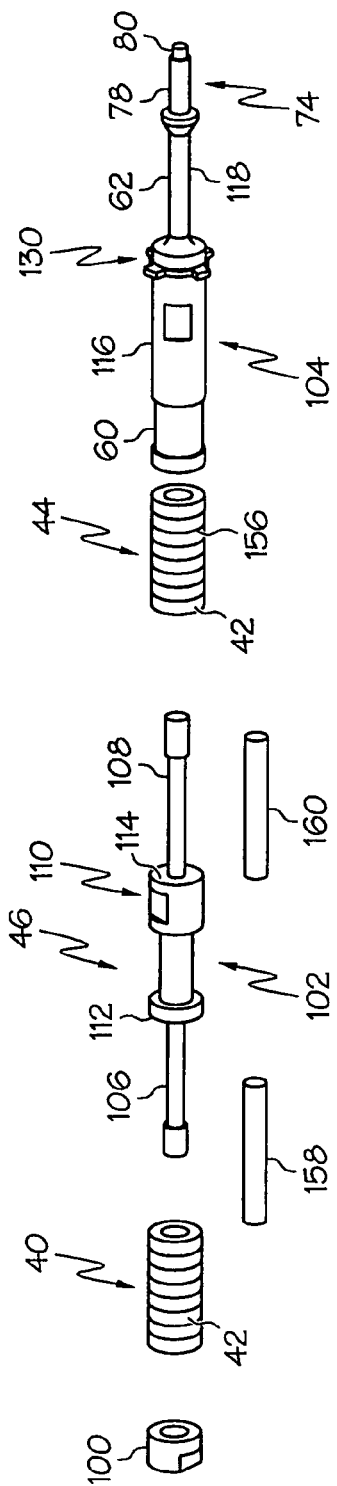

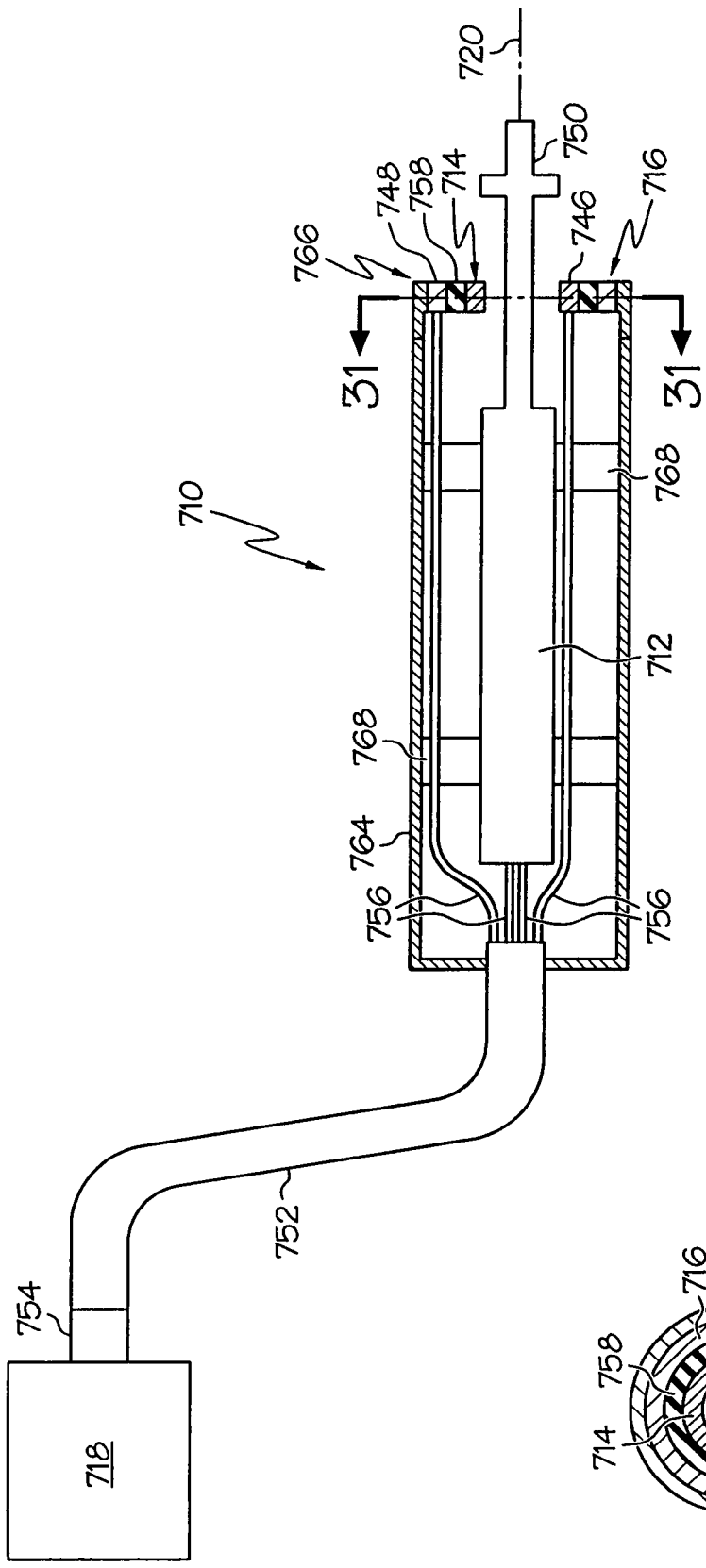

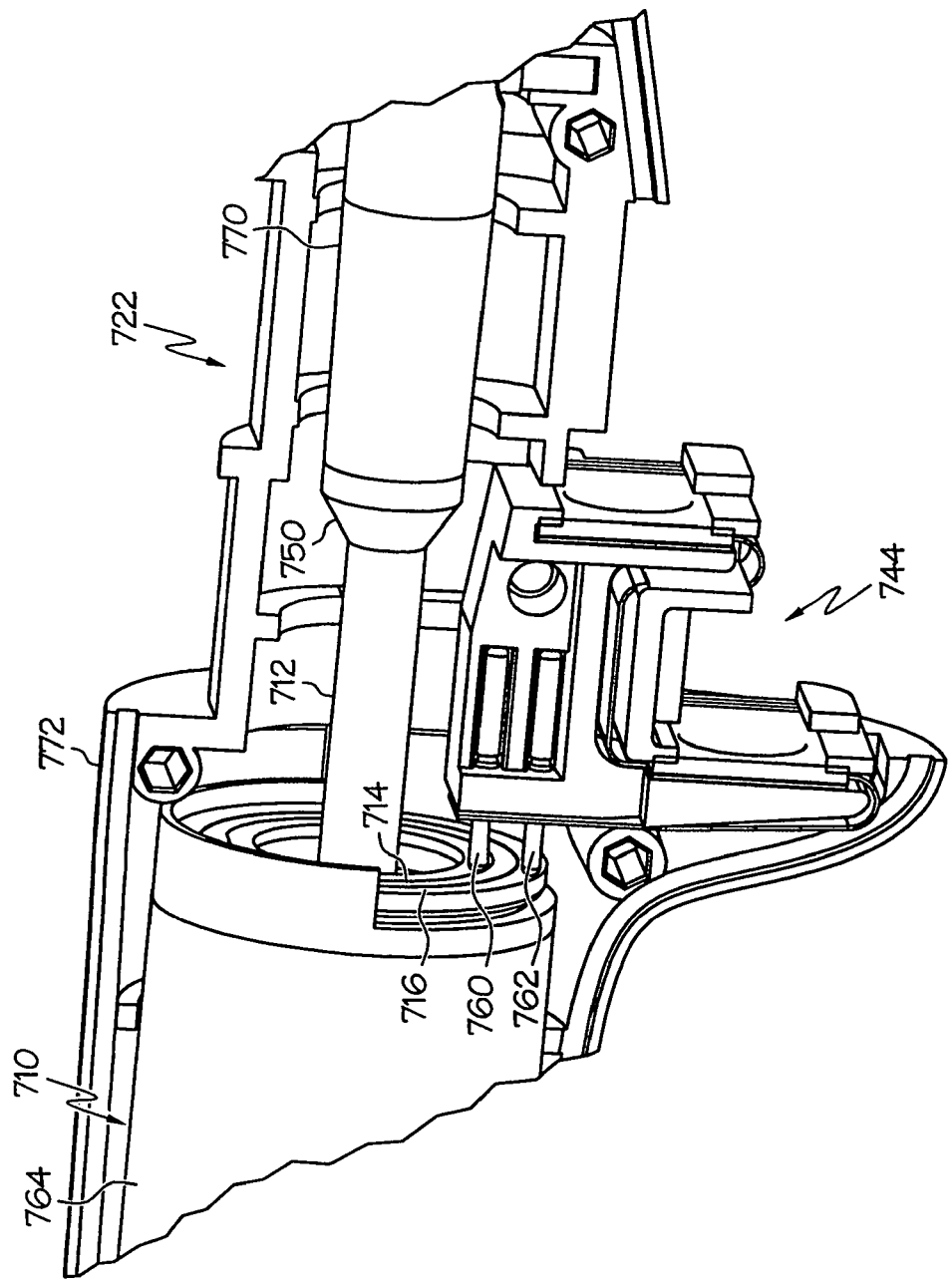

MEDICAL ULTRASOUND SYSTEM AND HANDPIECE AND METHODS FOR MAKING AND TUNING

CROSS REFERENCE TO RELATED APPLICATIONS

The present application is a divisional application of U.S. application Ser. No. 11/545,784 filed Oct. 10, 2006. The present application claims the priority benefit of U.S. provisional patent application Ser. No. 60/726,625, filed on Oct. 14, 2005.

FIELD OF THE INVENTION

The present invention is related generally to medical equipment, and more particularly to a medical ultrasound handpiece having a medical ultrasound transducer assembly, to a method for tuning the handpiece, to a method for making the transducer assembly, and to a medical ultrasound system including a handpiece and an ultrasonically-vibratable medical-treatment instrument which is attachable to the distal end portion of the transducer assembly of the handpiece.

BACKGROUND OF THE INVENTION

Medical ultrasound systems are known which include a medical ultrasound handpiece having a medical ultrasound transducer assembly and which include an ultrasonically-vibratable medical-treatment instrument attached to the distal end portion of the transducer assembly of the handpiece. Examples of such instruments include an ultrasonically vibrating scalpel and include an ultrasonic clamp having a first clamp arm which is an ultrasonically vibrating blade and having a second non-vibrating clamp arm. In one known application, the scalpel/blade vibrates at a fundamental frequency (i.e., a resonant frequency of displacement along the longitudinal axis of the instrument).

Conventional medical ultrasound systems provide the instrument with a desirable high displacement (i.e., a large vibrational amplitude) by employing a relatively large size transducer assembly resulting in a relatively large size handpiece which is unsuitable for a surgeon to hold and use in precise and delicate surgery.

Still, scientists and engineers continue to seek improved medical ultrasound handpieces having a medical ultrasound transducer assembly and improved systems and methods related thereto.

SUMMARY

A first expression of a first embodiment of the invention is for a medical ultrasound handpiece including a medical ultrasound transducer assembly. The transducer assembly includes consecutive first and second half-wave sections, wherein the first half-wave section includes a first node and the second half-wave section includes a second node. The first half-wave section includes a first piezoelectric transducer disk substantially centered about the first node, and the second half-wave section includes a second piezoelectric transducer disk substantially centered about the second node. The transducer assembly includes a gain stage located between the first and second piezoelectric transducer disks.

A first expression of a second embodiment of the invention is for a medical ultrasound handpiece including a medical ultrasound transducer assembly. The transducer assembly includes consecutive first and second half-wave sections, wherein the first half-wave section includes a first node and the second half-wave section includes a second node. The first half-wave section includes a first stacked plurality of piezoelectric transducer disks substantially centered about the first node, and the second half-wave section includes a second stacked plurality of piezoelectric transducer disks substantially centered about the second node. The transducer assembly includes a gain stage located between the first and second stacked pluralities of piezoelectric transducer disks.

A second expression of a second embodiment of the invention is for a medical ultrasound handpiece including a 1½-wave medical ultrasound transducer assembly. The transducer assembly includes consecutive first, second, and distal-most third half-wave sections, wherein the first half-wave section includes a first node, the second half-wave section includes a second node, and the third half-wave section includes a third node. The first half-wave section includes a first stacked plurality of piezoelectric transducer disks substantially centered about the first node, and the second half-wave section includes a second stacked plurality of piezoelectric transducer disks substantially centered about the second node. The transducer assembly includes a first, second, and third gain stages. The first gain stage is located in the first half-wave section distal the first stacked plurality of piezoelectric transducer disks. The second gain stage is located in the second half-wave section distal the second stacked plurality of piezoelectric transducer disks. The third gain stage extends distally from proximate the third node.

A first expression of a third embodiment of the invention is for a medical ultrasound handpiece including a 1-wave medical ultrasound transducer assembly. The transducer assembly includes consecutive first and distal-most second half-wave sections, wherein the first half-wave section includes a first node and the second half-wave section includes a second node. The first half-wave section includes a first stacked plurality of piezoelectric transducer disks, and the second half-wave section includes a second stacked plurality of piezoelectric transducer disks. The transducer assembly includes first and second gain stages, wherein the first gain stage is located in the first half-wave section distal the first stacked plurality of piezoelectric transducer disks, and wherein the second gain stage is located in the second half-wave section distal the second stacked plurality of piezoelectric transducer disks.

A first expression of a fourth embodiment of the invention is for a medical ultrasound handpiece including a 1½-wave medical ultrasound transducer assembly. The transducer assembly includes a proximal antinode, a distal antinode, and a node located between the proximal and distal antinodes. The transducer assembly includes a first stacked plurality of piezoelectric transducer disks located proximal the node, a second stacked plurality of piezoelectric transducer disks located distal the node, and a gain stage located distal the second stacked plurality of piezoelectric transducer disks.

A first expression of a fifth embodiment of the invention is for a medical ultrasound system including a medical ultrasound transducer assembly and an ultrasonically-vibratable medical-treatment instrument. The transducer assembly has a gain of unity and has a distal end portion. The instrument is attachable to the distal end portion of the transducer assembly and has at least one gain stage.

A first expression of a sixth embodiment of the invention is for a medical ultrasound system including a medical ultrasound transducer assembly and an ultrasonically-vibratable medical-treatment instrument. The transducer assembly has a distal end portion. The instrument is attachable to the distal end portion of the transducer assembly. The transducer assembly and the attached instrument together have an operating wavelength. The transducer assembly alone has a length which is at least equal to ¼ of the operating wavelength and which is less than ½ of the operating wavelength. The transducer assembly and the attached instrument together have a length equal to N times ½ of the operating wavelength, wherein N is a non-zero positive whole number.

A first expression of a seventh embodiment of the invention is for a medical ultrasound handpiece including a medical ultrasound transducer assembly. The transducer assembly has first and second nodes. The transducer assembly has a first transducer-assembly-to-housing mounting feature located proximate the first node and a second transducer-assembly-to-housing mounting feature located proximate the second node. The transducer assembly lacks any additional transducer-assembly-to-housing mounting feature.

A first expression of an eighth embodiment of the invention is for a medical ultrasound handpiece including a medical ultrasound transducer assembly and an annular connector assembly. The transducer assembly includes a metallic end-mass component, a piezoelectric transducer disk, and an electrode. The piezoelectric transducer disk is located distal the end-mass component and is in electrical contact with the electrode. The connector assembly surrounds the transducer assembly, is in electrical contact with the electrode, and is electrically connectable to an ultrasound electric generator.

A second expression of an eighth embodiment of the invention is for a medical ultrasound handpiece including a medical ultrasound transducer assembly and an annular connector assembly. The transducer assembly includes a metallic end-mass component, a stacked plurality of piezoelectric transducer disks, and electrodes. The stacked plurality of piezoelectric transducer disks is located distal the end-mass component. Each piezoelectric transducer disk is in electrical contact with a corresponding electrode. The connector assembly surrounds the transducer assembly, is in electrical contact with the electrodes, and is electrically connected to a cable socket which is electrically connectable to an ultrasound electric generator.

A first expression of a ninth embodiment of the invention is for a medical ultrasound handpiece including a medical ultrasound transducer assembly, an inner conductive ring, and an outer conductive ring. The transducer assembly is electrically connectable to an ultrasound electric generator, has a longitudinal axis, and is attachable to an ultrasonically-vibratable medical-treatment instrument having a switch which has an open position and a closed position. The inner conductive ring is substantially coaxially aligned with the longitudinal axis, circumferentially surrounds the transducer assembly, and has a distally-facing first annular surface. The outer conductive ring is substantially coaxially aligned with the longitudinal axis, circumferentially surrounds the transducer assembly, and has a distally-facing second annular surface. The outer conductive ring is electrically isolated from the inner conductive ring. The first and second annular surfaces are in electric contact with the switch of the attached instrument when the switch is in the closed position. The inner and outer conductive rings are electrically connectable to the generator, and the switch of the attached instrument controls the connected generator.

A first expression of a tenth embodiment of the invention is for a medical ultrasound handpiece including a medical ultrasound transducer assembly, a housing, a mount, and an annular bumper unit. The housing surrounds the transducer assembly. The mount pivotally attaches the transducer assembly to the housing. The bumper unit is attached to the housing and includes a plurality of spaced apart and inwardly projecting bumpers. None of the bumpers is in contact with the transducer assembly when the transducer assembly is not under a pivoting load. At least one of the bumpers is contact with the transducer assembly when the transducer assembly is under the pivoting load.

A first expression of an eleventh embodiment of the invention is for a medical ultrasound handpiece including a medical ultrasound transducer assembly, at least one mounting member, and a first housing component. The transducer assembly has a longitudinal axis and has a substantially coaxially aligned, circumferential surface groove. The at-least-one mounting member is at-least-partially-annular and has an inner portion located in the surface groove. The first housing component surrounds the transducer assembly and has a distal end portion including an annular longitudinally-facing surface with a recessed seat. The at-least-one mounting member has at least a proximal portion located in the seat.

Several benefits and advantages are obtained from one or more of the expressions of embodiments of the invention. In one example, one or more or all of the expressions of embodiments of the invention help enable a relatively small size medical ultrasound transducer assembly to provide an attached ultrasonically-vibratable medical-treatment instrument with a desirable high displacement (i.e., a large vibrational amplitude) resulting in a relatively small size handpiece which is suitable for a surgeon to hold and use in precise and delicate surgery.

BRIEF DESCRIPTION OF THE FIGURES

FIG. 3 is an exploded view of a portion of the handpiece of FIG. 2 showing the medical ultrasound transducer assembly, the bumper assembly, the housing, and the nose cone assembly of the handpiece of FIG. 2;

FIG. 4 is a view of the transducer assembly, the bumper assembly, and the nose cone assembly of FIG. 3, wherein the bumper assembly and the nose cone assembly are shown attached to the transducer assembly;

FIG. 5 is a perspective schematic view of the transducer assembly of FIG. 4 showing first and second stacked pluralities of piezoelectric transducer disks substantially centered about respective first and second nodes;

FIG. 6 is an exploded view of the transducer assembly of FIG. 5;

FIG. 30 is a schematic view of a ninth embodiment of the invention showing a medical ultrasound handpiece connected to an ultrasound electric generator, wherein portions of the handpiece are shown in cutaway;

FIG. 31 is a cross sectional view of the transducer assembly of the handpiece of FIG. 30 taken along lines 31-31 of FIG. 30;

FIG. 32 is a perspective view of a distal end portion of the handpiece of FIG. 30 connected to a proximal end portion of an ultrasonically-vibratable medical-treatment instrument which includes a switch which controls the generator;

DETAILED DESCRIPTION

Before explaining the several embodiments of the present invention in detail, it should be noted that each embodiment is not limited in its application or use to the details of construction and arrangement of parts and steps illustrated in the accompanying drawings and description. The illustrative embodiments of the invention may be implemented or incorporated in other embodiments, variations and modifications, and may be practiced or carried out in various ways. Furthermore, unless otherwise indicated, the terms and expressions employed herein have been chosen for the purpose of describing the illustrative embodiments of the present invention for the convenience of the reader and are not for the purpose of limiting the invention.

It is further understood that any one or more of the following-described expressions, embodiments, examples, etc. can be combined with any one or more of the other following-described expressions, embodiments, examples, etc.

Figure 1:
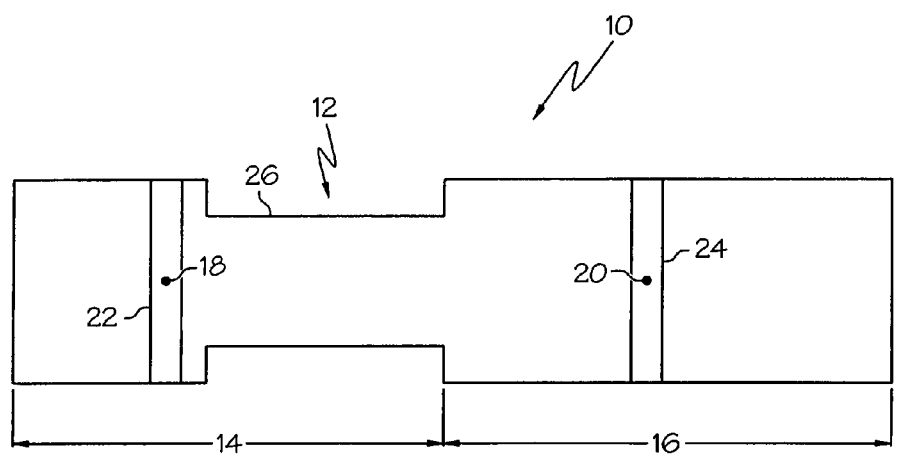
FIG. 1 is a schematic side elevational view of a first embodiment of the invention showing consecutive first and second half-wave sections of a medical ultrasound transducer assembly of a medical ultrasound handpiece, wherein a first piezoelectric transducer disk is substantially centered about a first node of the first half-wave section and a second piezoelectric transducer disk is substantially centered about a second node of the second half-wave section.
Figure 2:
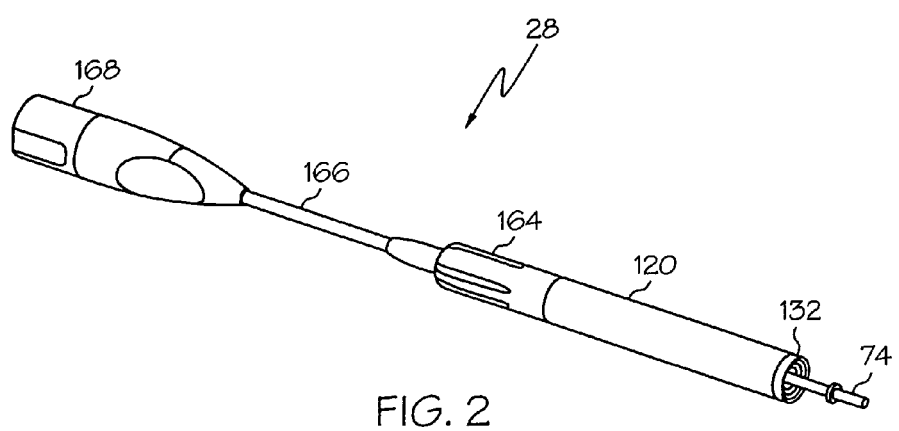
FIG. 2 is a perspective view of a second embodiment of the invention showing an assembled medical ultrasound handpiece including the exposed stud of the 1½-wave medical ultrasound transducer assembly of the handpiece.
Figure 7:
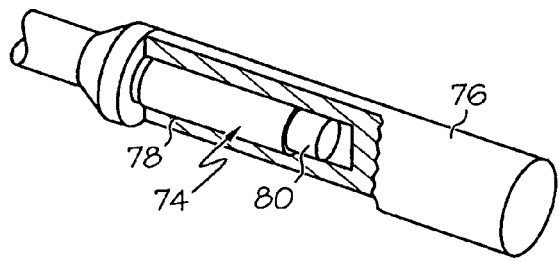
FIG. 7 is a perspective view of the stud of the transducer assembly of FIG. 2 with an ultrasonically-vibratable medical-treatment instrument attached thereto, wherein the instrument is shown in partial cutaway, and wherein the instrument is an ultrasonically vibratable scalpel.
Figure 8:
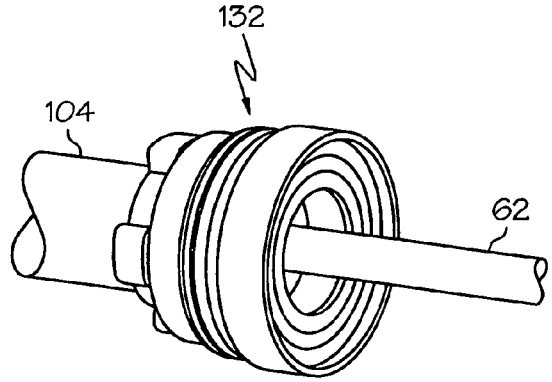
FIG. 8 is a perspective distal end view of a portion of the transducer assembly and of the nose cone assembly of FIG. 4.

A first embodiment of the invention is shown in FIG. 1. A first expression of the embodiment of FIG. 1 is for a medical ultrasound handpiece 10 including a medical ultrasound transducer assembly 12. The transducer assembly 12 includes consecutive first and second half-wave sections 14 and 16, wherein the first half-wave section 14 includes a first node 18 and the second half-wave section 16 includes a second node 20. The first half-wave section 14 includes a first piezoelectric transducer disk 22 substantially centered about the first node 18, and the second half-wave section 16 includes a second piezoelectric transducer disk 24 substantially centered about the second node 20. The transducer assembly 12 includes a gain stage 26 disposed between the first and second piezoelectric transducer disks 22 and 24.

It is noted, for the purpose of describing the various embodiments of the invention, that a medical ultrasound transducer assembly is a transducer assembly which ultrasonically vibrates an ultrasonically-vibratable medical-treatment instrument (such as, without limitation, an ultrasonic scalpel or an ultrasonic clamp), when attached to the transducer assembly, in a mode of vibration at a fundamental frequency (i.e., a fundamental resonant frequency), that a node is a node of vibration (i.e., a location of zero magnitude of vibration), and that an antinode is a location of maximum magnitude of vibration. Examples of modes of vibration include, without limitation, a longitudinal mode of vibration, a torsional mode of vibration, a bending mode of vibration, and a swelling mode of vibration, wherein the transducer assembly is not limited to operating in a single mode of vibration as is known to those skilled in the art. Also, the terminology "gain stage" means a positive gain stage and is a longitudinally-extending portion of the transducer assembly which results in increased magnitude of vibration. Gain stages may be provided by a portion of the transducer assembly having at least one of a reduced diameter (as identified in some of the figures), a (constant or non-constant) taper, or being of a different material, as is known to those skilled in the art. It is pointed out that piezoelectric transducer disks are not limited to those with an outer perimeter having a circular shape and may include those with an outer perimeter having another shape such as, without limitation, an elliptical shape.

A second embodiment of the invention is shown in FIGS. 2-13. A first expression of the embodiment of FIGS. 2-13 is for a medical ultrasound handpiece 28 including a medical ultrasound transducer assembly 30. The transducer assembly 30 includes consecutive first and second half-wave sections 32 and 34, wherein the first half-wave section 32 includes a first node 36 and the second half-wave section 34 includes a second node 38. The first half-wave section 32 includes a first stacked plurality 40 of piezoelectric transducer disks 42 substantially centered about the first node 36, and the second half-wave section 34 includes a second stacked plurality 44 of piezoelectric transducer disks 42 substantially centered about the second node 38. The transducer assembly 30 includes a gain stage 46 (also called a first gain stage) disposed between the first and second stacked pluralities 40 and 44 of piezoelectric transducer disks 42.

It is noted that, in one example, an electrode is disposed between adjacent piezoelectric transducer disks of a stacked plurality of piezoelectric transducer disks to energize the disks, as is known to those skilled in the art.

Figure 14:
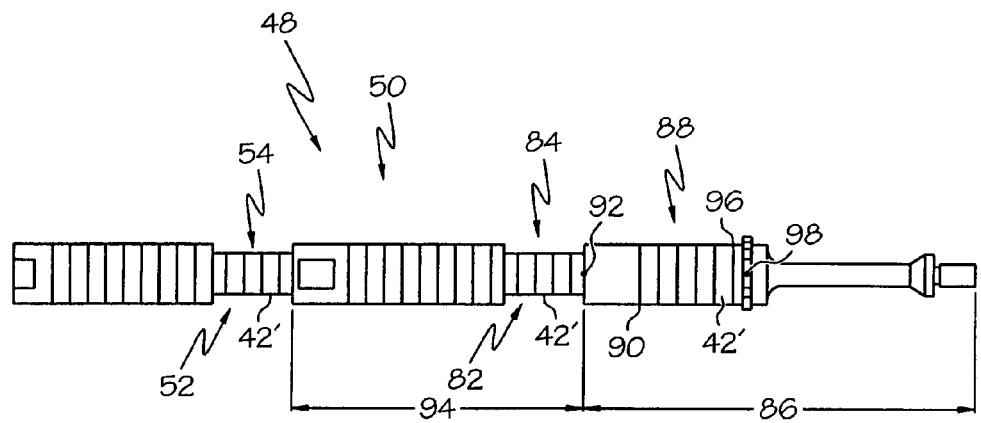
FIG. 14 is a side elevational schematic view of an alternate embodiment of a handpiece wherein the transducer assembly has first and second gain stages each including a stacked plurality of piezoelectric transducer disks.

In an alternate embodiment, as shown in FIG. 14, the handpiece 48 includes a transducer assembly 50, wherein the gain stage 52 (also called the first gain stage) of the transducer assembly 50 includes a stacked plurality 54 of piezoelectric transducer disks 42'. It is noted that the diameter of the piezoelectric transducer disks 42' of the gain stage 52 is smaller than the diameter of the piezoelectric transducer disks 42 of the first stacked plurality 40. It is also noted that a decrease in diameter at a node maximizes the gain of a gain stage, and that a following increase in diameter at a distally adjacent antinode fully keeps the gain of the gain stage.

A second expression of the embodiment of FIGS. 2-13 is for a medical ultrasound handpiece 28 including a 1½-wave medical ultrasound transducer assembly 30'. The transducer assembly 30' includes consecutive first, second, and distalmost third half-wave sections 32, 34, and 56, wherein the first half-wave section 32 includes a first node 36, the second half-wave section 34 includes a second node 38, and the third half-wave section 56 includes a third node 58. The first half-wave section 32 includes a first stacked plurality 40 of piezoelectric transducer disks 42 substantially centered about the first node 36, and the second half-wave section 34 includes a second stacked plurality 44 of piezoelectric transducer disks 42 substantially centered about the second node 38. The transducer assembly 30 includes first, second, and third gain stages 46, 60, and 62. The first gain stage 46 is disposed in the first half-wave section 32 distal the first stacked plurality 40 of piezoelectric transducer disks 42. The second gain stage 60 is disposed in the second half-wave section 34 distal the second stacked plurality 44 of piezoelectric transducer disks 42. The third gain stage 62 extends distally from proximate the third node 58.

It is noted that a 1½-wave transducer assembly is a transducer assembly having a length from its proximal end to its distal end of substantially 1½ wavelengths of its fundamental frequency. It is also noted that a 1½-wave transducer assembly has a proximal antinode at its proximal end (the proximal end of the first half-wave section), a common antinode of the first and second half-wave sections, a common antinode of the second and third half-wave sections, and a distal antinode at its distal end (the distal end of the third half-wave section).

In one enablement of the second expression of the embodiment of FIGS. 2-13, the first gain stage 46 has a proximal end 64 which is distally spaced apart from the first stacked plurality 40 of piezoelectric transducer disks 42 and has a distal end 65 which is disposed proximate a common antinode 66 of the first and second half-wave sections 32 and 34. In one variation, the second gain stage 60 has a proximal end 68 which is distally spaced apart from the second stacked plurality 44 of piezoelectric transducer disks 42 and has a distal end 70 which is disposed proximate a common antinode 72 of the second and third half-wave sections 34 and 56. In one modification, the third half-wave section 56 distally terminates in a stud 74 which is attachable to an ultrasonically-vibratable medical-treatment instrument 76. In one example, the stud 74 includes a proximal threaded portion 78 and includes a distal non-threaded portion 80 adjoining the proximal threaded portion 78, and the proximal threaded portion 78 is threadably attachable to the instrument 76. Examples of non-stud and/or non-threadable attachments are left to those skilled in the art.

In an alternate embodiment, as shown in FIG. 14, the first gain stage 52 includes a stacked plurality 54 of piezoelectric transducer disks 42', and the second gain stage 82 includes a stacked plurality 84 of piezoelectric transducer disks 42'. In one variation, the third half-wave section 86 includes a stacked plurality 88 of piezoelectric transducer disks 42' having a proximal end 90 which is distally spaced apart from the common antinode 92 of the second and third half-wave sections 94 and 86 and having a distal end 96 which is disposed proximate the third node 98.

A method for tuning the medical ultrasound handpiece 28 (wherein the handpiece 28 includes the stud 74) includes steps a) through c). Step a) includes measuring a fundamental frequency of the transducer assembly 30'. Step b) includes determining a desired fundamental frequency of the transducer assembly 30' wherein the desired fundamental frequency is greater than the measured fundamental frequency. Step c) includes machining at least the distal non-threaded portion 80 to match the measured fundamental frequency to the desired fundamental frequency to within a predetermined limit. In one variation, the machining of step c) shortens the non-threaded portion 80. In one modification, step c) also includes machining the proximal threaded portion 78. It is noted that the method is not limited to a 1½-wave transducer assembly.

A method for making an example of the transducer assembly 30' of the medical ultrasound handpiece 28 includes steps a) through g). In this method and example, there are first, second and third gain stages 46, 60 and 62, the first, second and third gain stages 46, 60 and 62 and the instrument 76 each have a gain, and the transducer assembly 30' has a design diameter. Step a) includes obtaining at least one electromechanical equation of an electromechanical requirement, of drive circuitry to drive the transducer assembly 30' with the attached instrument 76, which depends on the design diameter and the first, second and third gain stages 46, 60 and 62. Step b) includes obtaining at least one acoustic equation of an acoustic requirement, of stable dynamic behavior of the attached instrument 76, which depends on the design diameter, the first, second and third gain stages 46, 60 and 62, and the instrument gain. Step c) includes predetermining an acceptable range for each electromechanical requirement. Step d) includes predetermining an acceptable range for each acoustic requirement. Step e) includes preselecting the design diameter and the instrument gain. Step f) includes determining an acceptable first gain for the first gain stage 46, an acceptable second gain for the second gain stage 60, and an acceptable third gain for the third gain stage 62 using the at-least-one electromechanical equation and the at-least-one acoustic equation which place each electromechanical requirement in the acceptable range for that electromechanical requirement and each acoustic requirement in the acceptable range for that acoustic requirement. Step g) includes constructing the transducer assembly 30' with the first gain stage 46 having the determined acceptable first gain, with the second gain stage 60 having the determined acceptable second gain, and with the third gain stage 62 having the determined acceptable third gain. It is noted that the design diameter is a basic diameter of the transducer assembly and does not reflect any diameter of a gain stage, any torquing flat on a component, any mounting flange of the transducer assembly to a housing, any seat of a stud which engages an instrument, and any diameter of a non-threaded portion of such stud. It is also noted that the method is not limited to a 1½-wave transducer assembly and/or to three gain stages and/or particular component composition.

In one employment of the method for making the transducer assembly 30', the attached instrument 76 has a fundamental frequency. In this employment, step a) obtains an equation of the phase margin of the attached instrument 76, an equation of the power dissipation of the transducer assembly 30', an equation of the displacement (linear or angular depending on the mode of vibration) of the attached instrument 76, an equation of the impedance of the transducer assembly 30', an equation of the power transmitted to patient tissue (tissue power) by the attached instrument 76, and an equation of the loaded maximum phase of the attached instrument 76. It is noted that the phrase phase margin, power dissipation, displacement, tissue power, impedance, and loaded maximum phase are examples of electromechanical requirements each having an acceptable range for drive circuitry in an ultrasonic electric generator to drive the transducer assembly 30' with the attached instrument 76. In this employment, step b) obtains an equation of a first resonant frequency (Sn−1) next below the fundamental frequency, obtains an equation of a second resonant frequency (Sn+1) next above the fundamental frequency, and obtains an equation of the span (Span−1) of the first and second resonant frequencies. It is noted that Sn−1, Sn+1, and Span-1 are examples of acoustic requirements each having an acceptable range for stable dynamic behavior of the attached instrument 76.

An example of a set of such at-least-one electromechanical equation for the transducer assembly 30' is as follows:

Phase Margin=4284.8+72.71*DD−422.6*TG−2488.5*HG−505.74*MG+513.4*(HG)$^2$+26.1*(MG)$^2$−62.8*(DD*HG)+7.44*(DD*MG)+188.9*(TG*HG)+75.3*(HG*MG);

Power Dissipation=21.22−0.905*DD−0.784*TG−12.3*HG−5.7*MG+2.1*(HG)$^2$+0.11*(MG)$^2$+0.021*(DD*HG)+0.37*(DD*MG)+0.75*(TG*HG)+1.75*(HG*MG);

Displacement=70.62−7.15*DD−0.382*TG−26.44*HG−14.12*MG+2.29*(HG)$^2$−0.12*(MG)$^2$+1.48*(DD*HG)+1.47*(DD*MG)+1.42*(TG*HG)+4.90*(HG*MG);

Tissue Power=253.1+19.49*DD−17.6*TG−108.93*HG−40.8*MG+21.9*(HG)$^2$+4.5*(MG)$^2$−6.44*(DD*HG)−2.7*(DD*MG)+6.7*(TG*HG)+5.7*(HG*MG);

Impedance=194.82−8.31*DD−7.2*TG−112.78*HG−52.1*MG+18.98*(HG)$^2$+0.97*(MG)$^2$+0.19*(DD*HG)+3.4*(DD*MG)+6.84*(TG*HG)+16.1*(HG*MG); and Loaded Maximum Phase=268.9+1.225*DD−6.5*TG−157.5*HG−38.7*MG+29.9*(HG)$^2$+3.23*(MG)$^2$.

An example of a set of such at-least-one acoustic equation for the transducer assembly 30' is as follows:

Sn+1=163.5*DD+228.5*IG+4001.6*TG+2149.6*HG+860.3*MG+500.5*(IG)$^2$−1037.9*(IG*TG)−454.1*(IG*HG)−231.3*(IG*MG)−9125.7;

Sn+1=2805.6*DD−1590.3*IG+34.4*TG+1465.6*HG+2652.4*MG−168.1*(DD)$^2$+447.9*(IG)$^2$−1.38.2*(MG)$^2$−229.6*(IG*MG)−437.8*(HG*MG)−15212.6; and Span−1=3713.9*DD−2906.9*IG+2757.1*TG+274.7*HG+3160.6*MG−214.6*(DD)$^2$+976.2*(IG)$^2$−190*(MG)$^2$−672.5*(IG*TG)−460.9*(IG*MG)−19879.9.

In the above nine equations, the design diameter DD is the diameter (in millimeters) of the end-mass component 100 (which is equal to the outer diameter of the piezoelectric transducer disks 42 of the first and second stacked pluralities 40 and 44 of piezoelectric transducer disks 42), IG is the instrument gain, the trans gain TG is the first gain, the horn gain HG is the second gain, and the mount gain MG is the third gain; It is noted that the design diameter is also the basic diameter of the transducer assembly 30' as shown in FIG. 5. The units for the phase margin are Hertz, for the power dissipation are watts, for the displacement are microns (peak-to-peak), for the tissue power are watts, for the impedance are ohms, for the loaded maximum phase are degrees, for Sn−1 are Hertz, for Sn+1 are Hertz, and for Span−1 are Hertz. The above nine equations were developed for a particular example of the transducer assembly 30' wherein a discussion of some of the characteristics of the particular transducer assembly follows. The particular transducer assembly 30' operated in a longitudinal mode of vibration and included a metallic end-mass component 100 consisting essentially of stainless steel, a metallic transducer-horn component 102 consisting essentially of titanium, and a metallic horn-mount component 104 consisting essentially of titanium. The particular transducer assembly included eight PZT (piezoelectric transducer), type 8 material disks in each stack (PZT disk dimensions were: outside diameter (DD in the equations); 4.2 mm inside diameter; and 2.34 mm thick). The PZT inside diameter was 0.5 mm (millimeters) radially separated from the metal parts. The stud had 6-32 USC threads. Each half wave was tuned to a longitudinal fundamental frequency close to 55.5 KHz (kilo-Hertz). Using the above nine equations, applicants successfully built and tested a particular transducer assembly in which DD was chosen to be 8 mm.

One technique for developing a similar set of nine equations for a different transducer assembly including, for example and without limitation, different component composition and/or a different mode (or mixed modes) of vibration and/or piezoelectric transducer disks with non-circular outer perimeters and/or a transducer assembly having a different number of half-wave sections and/or a transducer assembly having a different number of gain stages, etc., is hereinafter described. Start by selecting a statistical design such as Box-Behnken design of experiments, in which: (1) the factors (i.e., independent variables) are the design diameter of the transducer assembly, the gain stages of the transducer assembly, and the instrument gain; (2) the responses for acoustic (dynamic) performance (i.e., the acoustic-performance independent variables) are Sn+1, Sn−1, and Span−1; and (3) the responses for electromechanical performance (i.e., the electromechanical independent variables) are impedance, phase margin, tissue power, power dissipation, displacement and loaded maximum phase. Create the experiment by selecting the ranges of factors. Using commercial finite element analysis software such as Abaqus, IDEAS etc, solve cases in the experiment for finite element models of the transducer assembly. Analyze the data using commercial statistical software such as Minitab to develop the equations relating the responses to the factors. Simultaneously solve the equations to size the gain stages for delivering a desired acoustic performance with a particular attached instrument and a desired electromechanical performance with a particular connected generator. Using this methodology, a person skilled in the art can develop equations, without undue experimentation, for any transducer assembly including, for example, any fundamental vibrational mode of interest (longitudinal, torsion, bending, swelling etc.), any design cross section (including a non-circular cross section), any PZT type, any metal used for metal parts, etc. It is noted that, in a particular application, all equations of the set of nine equations would or would not be used and/or at least one different acoustic performance equation and/or different electromechanical performance equation would be included. A person skilled in the art may use different factors and responses in one or both of the electromechanical performance and the acoustic performance.

In a first design of the second expression of the embodiment of FIGS. 2-13, the medical ultrasound handpiece 28 includes a metallic end-mass component 100, a metallic transducer-horn component 102, and a metallic horn-mount component 104. The piezoelectric transducer disks 42 of the first and second stacked pluralities 40 and 44 of piezoelectric transducer disks 42 are annular disks, and the transducer-horn component 102 has proximal and distal portions 106 and 108. The piezoelectric transducer disks 42 of the first stacked plurality 40 of piezoelectric transducer disks 42 surround the proximal portion 106 of the transducer-horn component 102, and the piezoelectric transducer disks 42 of the second stacked plurality 44 of piezoelectric transducer disks 42 surround the distal portion 108 of the transducer-horn component 102.

In one variation of the first design, the transducer-horn component 102 has an intermediate portion 110. The intermediate portion 110 includes the first gain stage 46 and includes proximal and distal seat portions 112 and 114 bounding the first gain stage 46. The end-mass component 100 is disposed proximal the first stacked plurality 40 of piezoelectric transducer disks 42. The end-mass component 100 is threadably attached to the proximal portion 106 of the transducer-horn component 102 compressing the first stacked plurality 40 of piezoelectric transducer disks 42 against the proximal seat portion 112. In one construction, torquing flats on the end-mass component 100 and on the transducer-horn component 102 facilitate such compression.

In one modification of the first design, the horn-mount component 104 is disposed distal the second stacked plurality 44 of piezoelectric transducer disks 42. The horn-mount component 104 is threadably attached to the distal portion 108 of the transducer-horn component 102 compressing the second stacked plurality 44 of piezoelectric transducer disks 42 against the distal seat portion 114. In one construction, torquing flats on the horn-mount component 104 and on the transducer-horn component 102 facilitate such compression. In one example, the horn-mount component 104 has a proximal portion 116 which includes the second gain stage 60 and has a distal portion 118 which includes the third gain stage 62.

In one implementation of the second expression of the embodiment of FIGS. 2-13, the medical ultrasound handpiece 28 includes a housing 120 (also called a mid housing), wherein the housing 120 surrounds the transducer assembly 30'. In one variation, the medical ultrasound handpiece 28 includes an annular bumper assembly 122 having a plurality of spaced apart and inwardly projecting bumpers 124. The bumper assembly 122 surrounds the first stacked plurality 40 of piezoelectric transducer disks 42, wherein the bumpers 124 are in contact with the first stacked plurality 40 of piezoelectric transducer disks 42 proximate the first node 36, and the housing 120 is in surrounding contact with the bumper assembly 122.

In one arrangement of the second expression of the embodiment of FIGS. 2-13, the transducer assembly 30' has a longitudinal axis 126, the housing 120 has a multi-lug inward flange 128, and the horn-mount component 104 has a multi-lug outward flange 130 disposed proximate the third node 58 (and distal the multi-lug inward flange 128 after first aligning the lugs for passage and then relatively rotating for non-passage). In this arrangement, the handpiece 28 includes a nose cone assembly 132 having a dielectric multi-lug ring 134 (such as, but not limited to, a compressed, soft elastomeric, vibration isolating, multi-lug ring) disposed longitudinally between (after first aligning the lugs for passage and then relatively rotating for non-passage) and in contact with the multi-lug inward and outward flanges 128 and 130 and covering and contacting the multi-lug outward flange 130. In this arrangement, the housing 120 is in surrounding contact with the multi-lug ring 134.

Figure 9:
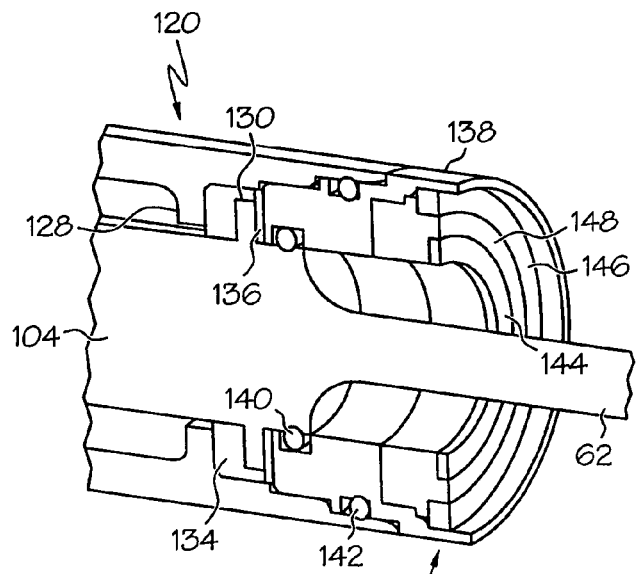
FIG. 9 is a cross sectional view of the transducer assembly and of the nose cone assembly of FIG. 8.
Figure 10:
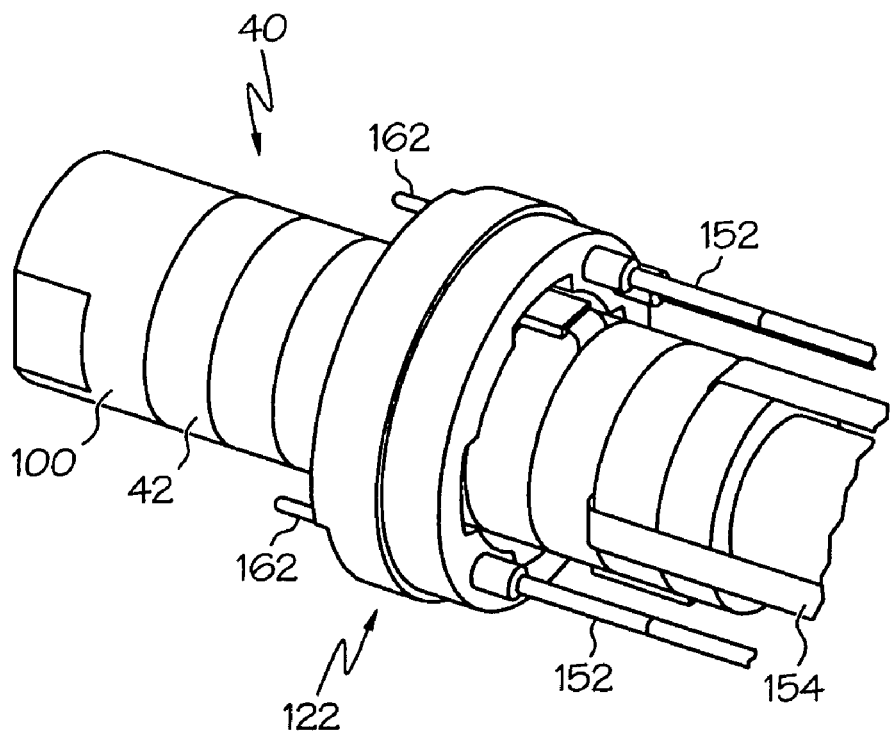
FIG. 10 a view of a portion of the transducer assembly of FIG. 4 with the attached bumper assembly.
Figure 11:
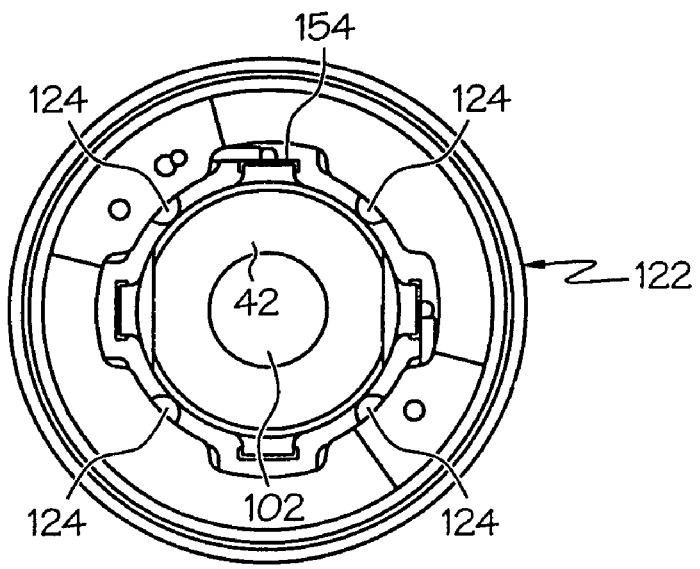
FIG. 11 is a cross sectional view of the bumper assembly of FIG. 10.
Figure 12:
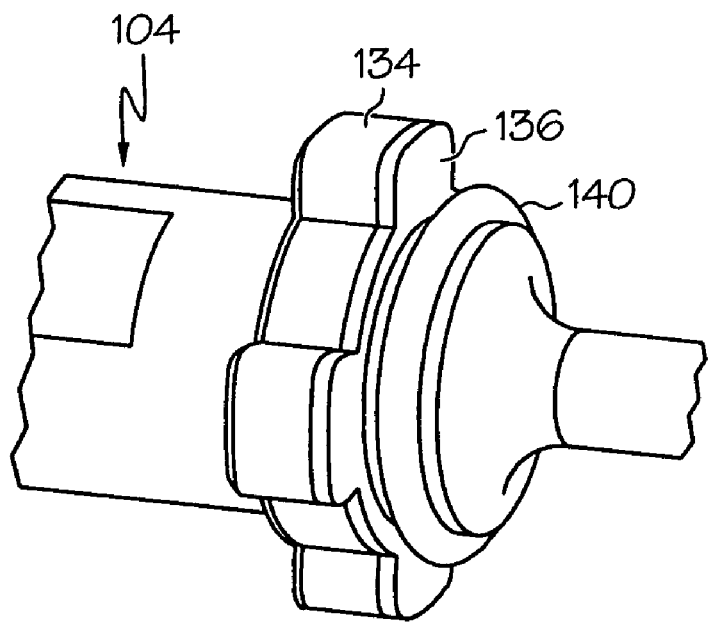
FIG. 12 is a perspective view of a portion of the transducer assembly and of the dielectric multi-lug ring, the dielectric washer, and the first O-ring seal of the nose cone assembly of FIG. 9.
Figure 13:
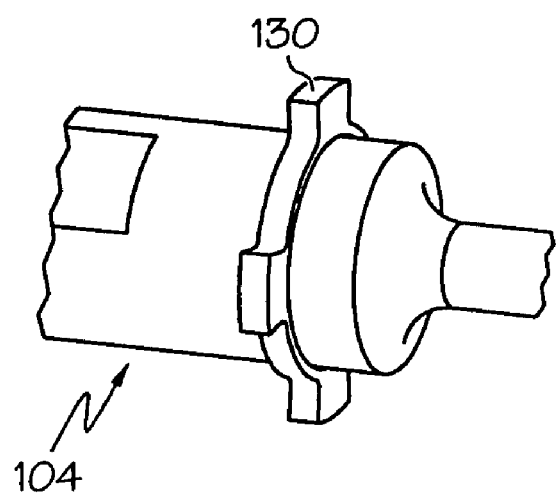
FIG. 13 is a perspective view of the transducer assembly of FIG. 12.

In one example, the nose cone assembly 132 includes a longitudinally-compressed dielectric washer 136 (such as, but not limited to, an elastomeric washer) distally abutting the multi-lug outward flange 130 and includes an annular nose cone 138 distally abutting the washer 136. In this example, the housing 120 is in surrounding contact with the nose cone 138. In one variation, the nose cone assembly 132 includes first and second O-ring seals 140 and 142 as shown in FIGS. 3 and 9. In one modification, the nose cone assembly 132 includes inner and outer conductive (electrically conductive) rings 144 and 146 separated by an annular dielectric member 148 as shown in FIG. 9.

In the same example, the outer conductive ring 146 contacts the housing 120 and is a ground (electrical ground) ring, and the inner conductive ring 144 is a hot (electrically hot) ring electrically connectable (in part by wiring 150) to a low AC output of an ultrasound electric generator (not shown). The instrument 76 has a switch (not shown) which is electrically connected to the inner and outer conductive rings 144 and 146 when the instrument 76 is attached to the stud 74. The switch controls the ultrasound electric generator. In other arrangements, not shown, the inner and outer conductive rings 144 and 146 are omitted, and the ultrasound electric generator has an onboard switch or the handpiece has a switch.

In the same example, the generator has positive and negative high AC outputs electrically connectable (in part by wiring 152 and jumpers 154) to electrodes 156 disposed between adjacent piezoelectric transducer disks 42. The piezoelectric transducer disks 42 of the first stacked plurality 40 of piezoelectric transducer disks 42 are radially-inwardly electrically isolated from the transducer-horn component 102 by a first dielectric cylinder 158. The piezoelectric transducer disks 42 of the second stacked plurality 44 of piezoelectric transducer disks 42 are radially-inwardly electrically isolated from the transducer-horn component 102 by a second dielectric cylinder 160. It is noted that the stud 74 extends distally of the nose cone assembly 132, and that a proximal end portion of the nose cone 138 is disposed inside, and press fitted to, a distal end portion of the housing 120.

In the same example, the bumper assembly 122 includes pins 162 from which the wiring 152 extends to the electrodes/jumpers 156/154 to power the piezoelectric transducer disks 42. In one variation, the handpiece 28 includes an annular end cap 164 having pins (not shown) which engage the pins 162 of the bumper assembly 122 when a distal end portion of the end cap 164 is disposed outside, and press fitted to, a proximal end portion of the housing 120. This causes the bumper assembly 122 to be longitudinally secured between an inner annular seat (not shown) of the housing 120 and an inner annular seat (not shown) of the end cap 164.

In the same example, the handpiece 28 includes a cable 166 containing the wiring 150 and the wiring 152. The cable 166 extends from a proximal end portion of the end cap 164 to a proximal plug 168. The plug 168 is electrically connectable to an ultrasound electric generator (not shown).

Figure 15:
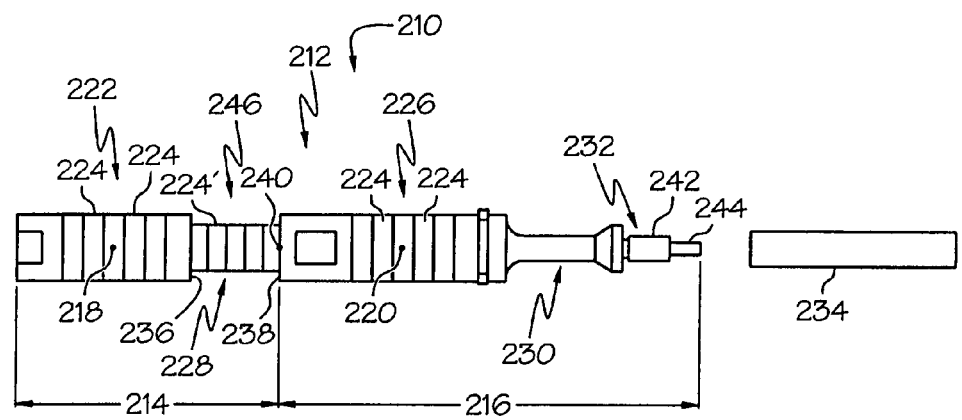
FIG. 15 is a side elevational schematic view of a third embodiment of the invention showing a 1-wave medical ultrasound transducer assembly of a medical ultrasound handpiece and showing an ultrasonically-vibratable medical-treatment instrument which is attachable to the stud of the transducer assembly.

A third embodiment of the invention is shown in FIG. 15. A first expression of the embodiment of FIG. 15 is for a medical ultrasound handpiece 210 including a 1-wave medical ultrasound transducer assembly 212. The transducer assembly 212 includes consecutive first and distal-most second half-wave sections 214 and 216, wherein the first half-wave section 214 includes a first node 218 and the second half-wave section 216 includes a second node 220. The first half-wave section 214 includes a first stacked plurality 222 of piezoelectric transducer disks 224 and the second half-wave section 216 includes a second stacked plurality 226 of piezoelectric transducer disks 224. The transducer assembly 212 includes first and second gain stages 228 and 230, wherein the first gain stage 228 is located in the first half-wave section 214 distal the first stacked plurality 222 of piezoelectric transducer disks 224, and wherein the second gain stage 230 is located in the second half-wave section 216 distal the second stacked plurality 226 of piezoelectric transducer disks 224.

In one enablement of the first expression of the embodiment of FIG. 15, the second half-wave section 216 distally terminates in a stud 232 which is attachable to an ultrasonically-vibratable medical-treatment instrument 234. In one variation, the stud 232 includes a proximal threaded portion 242 and includes a distal non-threaded portion 244 adjoining the proximal threaded portion 242, wherein the proximal threaded portion 242 is threadably attachable to the instrument 234. Examples of non-stud and/or non-threadable attachments are left to those skilled in the art. A method for tuning the handpiece 210 is identical to the previously described method for tuning the handpiece 28.

In one arrangement of the first expression of the embodiment of FIG. 15, the first stacked plurality 222 of piezoelectric transducer disks 224 is substantially centered about the first node 218, and the second stacked plurality 226 of piezoelectric transducer disks 224 is disposed proximal the second node 220. In one variation, the first gain stage 228 has a proximal end 236 which is distally spaced apart from the first stacked plurality 222 of piezoelectric transducer disks 224 and has a distal end 238 which is disposed proximate a common antinode 240 of the first and second half-wave sections 214 and 216. In one example, the first gain stage 228 includes a stacked plurality 246 of piezoelectric transducer disks 224'. In another example, not shown, the first gain stage lacks any piezoelectric transducer disks. It is noted that an operating handpiece 210 will have a proximal antinode at the proximal end of the transducer assembly 212 and a distal antinode at the distal end of the transducer assembly 212.

Figure 16:
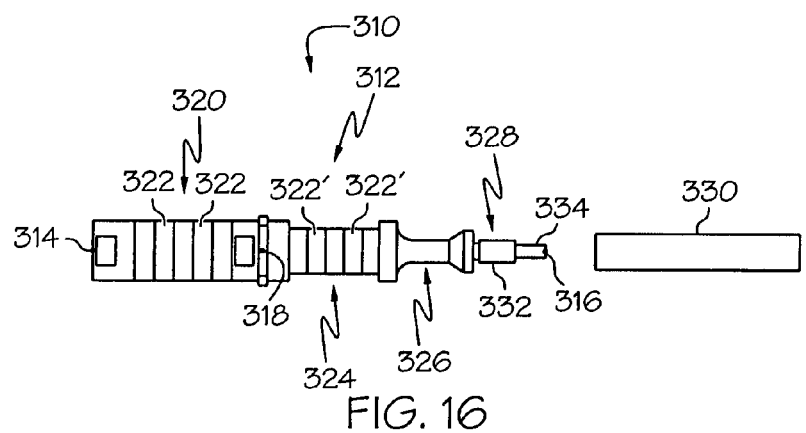
FIG. 16 is a side elevational schematic view of a fourth embodiment of the invention showing a ½-wave medical ultrasound transducer assembly of a medical ultrasound handpiece and showing an ultrasonically-vibratable medical-treatment instrument which is attachable to the stud of the transducer assembly.

A fourth embodiment of the invention is shown in FIG. 16. A first expression of the embodiment of FIG. 16 is for a medical ultrasound handpiece 310 including a ½-wave medical ultrasound transducer assembly 312. The transducer assembly 312 includes a proximal antinode 314, a distal antinode 316, and a node 318 located between the proximal and distal antinodes 314 and 316. The transducer assembly 312 includes a first stacked plurality 320 of piezoelectric transducer disks 322 located proximal the node 318, a second stacked plurality 324 of piezoelectric transducer disks 322' located distal the node 318, and a gain stage 326 located distal the second stacked plurality 324 of piezoelectric transducer disks 322'.

In one enablement of the first expression of the embodiment of FIG. 16, the transducer assembly 312 distally terminates in a stud 328 which is attachable to an ultrasonically-vibratable medical-treatment instrument 330. In one variation, the stud 328 includes a proximal threaded portion 332 and includes a distal non-threaded portion 334 adjoining the proximal threaded portion 332, wherein the proximal threaded portion 332 is threadably attachable to the instrument 330. Examples of non-stud and/or non-threadable attachments are left to those skilled in the art. A method for tuning the handpiece 310 is identical to the previously described method for tuning the handpiece 28.

Figure 17:
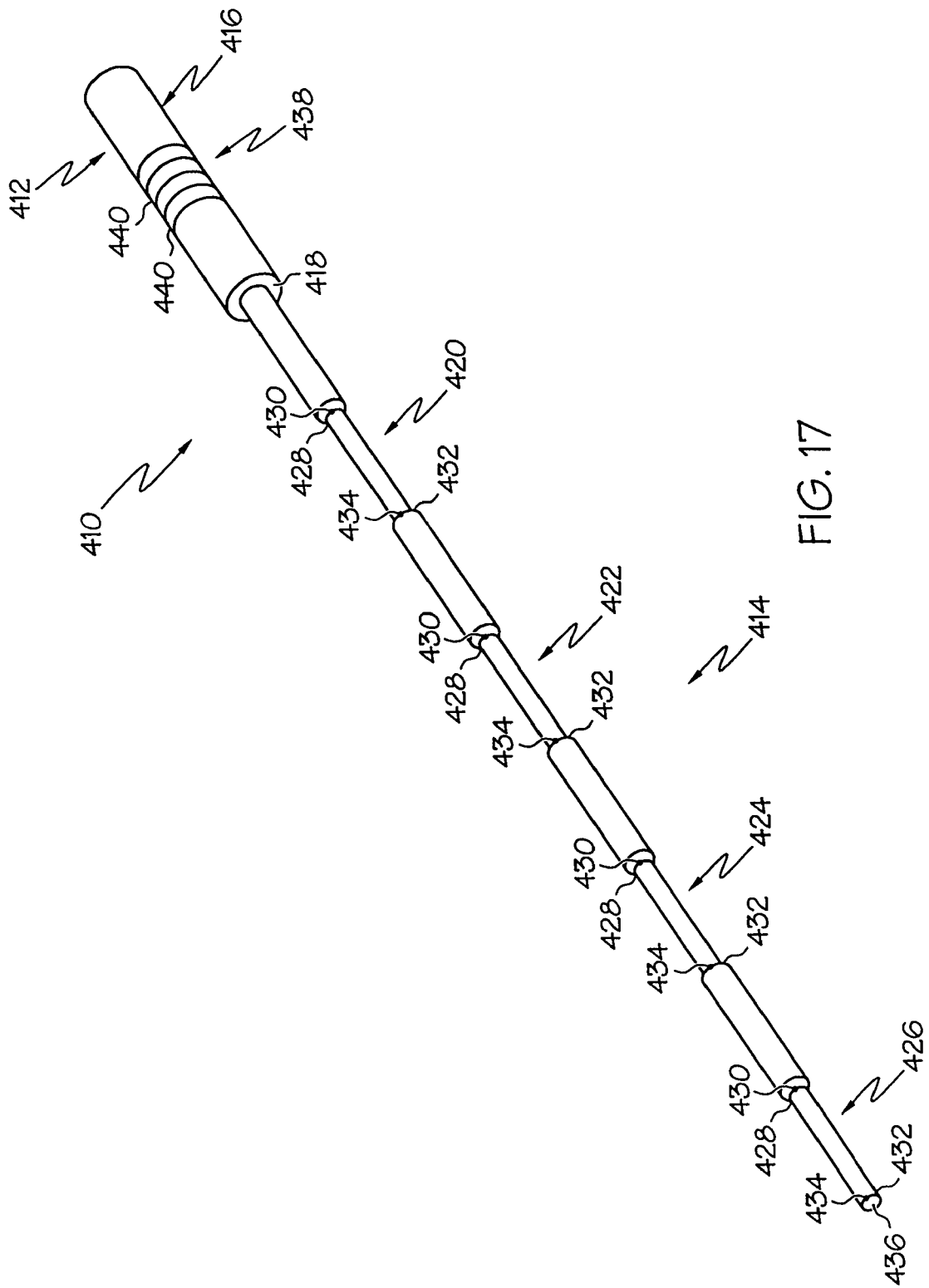
FIG. 17 is a perspective view of a fifth embodiment of the invention showing a medical ultrasound system including a medical ultrasound transducer assembly having a unity-gain and including an ultrasonically-vibratable medical-treatment instrument having four gain stages.

A fifth embodiment of the invention is shown in FIG. 17. A first expression of the embodiment of FIG. 17 is for a medical ultrasound system 410 including a medical ultrasound transducer assembly 412 and an ultrasonically-vibratable medical-treatment instrument 414. The transducer assembly 412 has a gain of unity and has a distal end portion 418. The instrument 414 is attachable (and in one example is attached) to the distal end portion 418 of the transducer assembly 412 and has at least one gain stage 420, 422, 424 and 426.

In one enablement of the first expression of the embodiment of FIG. 17, the at-least-one gain stage 420, 422, 424 and 426 includes a plurality of gain stages 420, 422, 424 and 426. In one variation, each gain stage 420, 422, 424 and 426 has a proximal end 428 disposed proximate a corresponding node 430 of the instrument 414 and has a distal end 432 disposed proximate a corresponding antinode 434 of the instrument to maximize the displacement at the distal end 436 of the instrument 414. In one implementation of the embodiment of FIG. 17, the transducer assembly 412 includes a stacked plurality 438 of piezoelectric transducer disks 440. In one example, the (unity gain) transducer assembly 412 should have less quiescent power and heat than a high gain transducer assembly and should provide for better sealing (because of less nodal vibration) than a high gain transducer assembly. In the same or a different example, the (unity gain) transducer assembly 412 should provide for a smaller handpiece 412 and should provide the potential for quick connection of an instrument 414 (such as a scalpel) to the handpiece 412.

Figure 18:
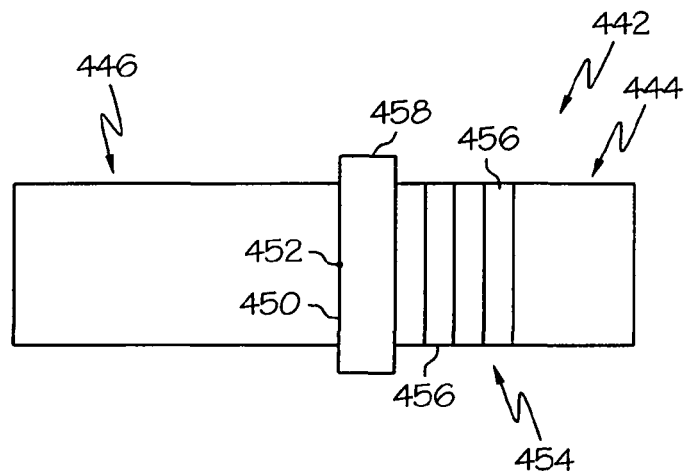
FIG. 18 is a side elevational schematic view of a sixth embodiment of the invention showing a medical ultrasound system including a medical ultrasound transducer assembly and an ultrasonically-vibratable medical-treatment instrument which together have an operating wavelength, wherein the transducer assembly alone has a length which is less than ½ of the operating wavelength.

A sixth embodiment of the invention is shown in FIG. 18. A first expression of the embodiment of FIG. 16 is for a medical ultrasound system 442 including a medical ultrasound transducer assembly 444 and an ultrasonically-vibratable medical-treatment instrument 446. The transducer assembly 444 has a distal end portion 450. The instrument 446 is attachable (and in one example is attached) to the distal end portion 450 of the transducer assembly 444. The transducer assembly 444 and the attached instrument 446 together have an operating wavelength. The transducer assembly 444 alone has a length which is at least equal to ¼ of the operating wavelength and which is less than ½ of the operating wavelength. The transducer assembly 444 and the attached instrument 446 together have a length equal to N times ½ of the operating wavelength, wherein N is a non-zero positive whole number.

In one enablement of the first expression of the embodiment of FIG. 18, N equals one. In one variation, the transducer assembly 444 and the attached instrument 446 together have a node 452, and the transducer assembly 444 includes the node 452. In one modification, the transducer assembly 444 includes a stacked plurality 454 of piezoelectric transducer disks 456. In one example, the transducer assembly 444 includes a flange 458 disposed proximate the node 452. In a first construction, the flange 458 is disposed proximal the node 452 with the instrument 446 attached to the flange 458 and with the stacked plurality 454 of piezoelectric transducer disks 456 disposed proximal and abutting the flange 458.

Figure 19:
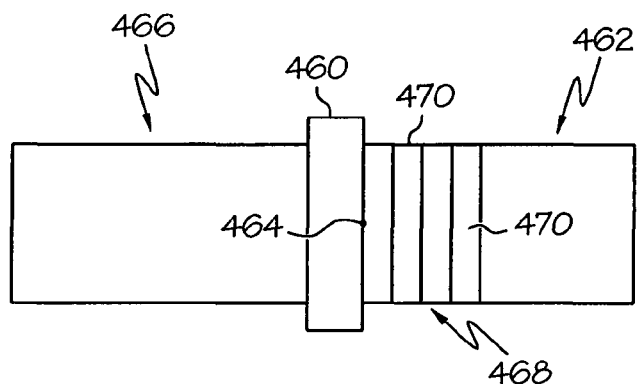
FIGS. 19 and 20 are side elevational schematic views of alternate embodiments of the system of FIG. 18.
Figure 20:
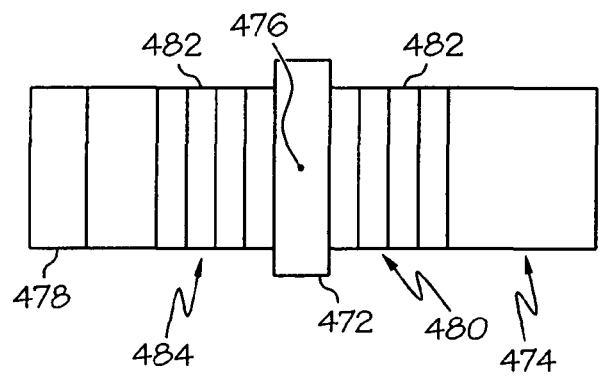

In a second construction, as shown in alternate embodiment of FIG. 19, the flange 460 of the transducer assembly 462 is disposed distal the node 464 with the instrument 466 attached to the flange 460 and with the stacked plurality 468 of piezoelectric transducer disks 470 disposed proximal and abutting the flange 460. In a third construction, as shown in the alternate embodiment of FIG. 20, the flange 472 of the transducer assembly 474 is substantially centered at the node 476 with the instrument 478 attached to the flange 472, with the stacked plurality 480 of piezoelectric transducer disks 482 disposed proximal and abutting the flange 472, and with an additional stacked plurality 484 of piezoelectric transducer disks 482 disposed distal and abutting the flange 472.

Figure 21:
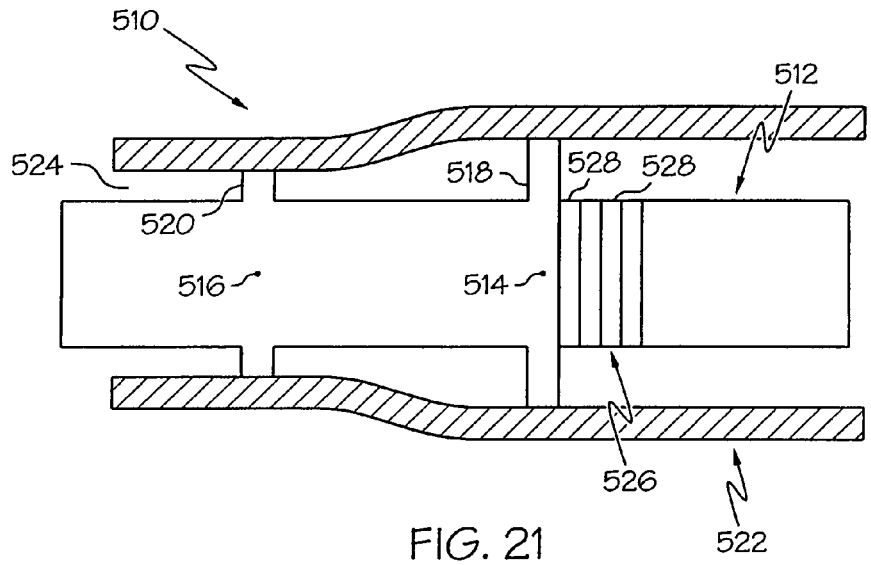
FIG. 21 is a side elevational schematic view of a seventh embodiment of the invention showing a medical ultrasound handpiece including a medical ultrasound transducer assembly and a housing, wherein the transducer assembly has a first transducer-assembly-to-housing mounting feature disposed proximate a proximal node of the transducer assembly and has a second transducer-assembly-to-housing mounting feature disposed proximate a distal node of the transducer assembly.

A seventh embodiment of the invention is shown in FIG. 21. A first expression of the embodiment of FIG. 21 is for a medical ultrasound handpiece 510 including a medical ultrasound transducer assembly 512. The transducer assembly 512 has proximal and distal nodes 514 and 516. The transducer assembly 512 has a first transducer-assembly-to-housing mounting feature 518 disposed proximate the proximal node 514 and a second transducer-assembly-to-housing mounting feature 520 disposed proximate the distal node 516. The transducer assembly 512 lacks any additional transducer-assembly-to-housing mounting feature.

In one enablement of the first expression of the embodiment of FIG. 21, the handpiece 510 includes a housing 522 having an opening 524 and surrounding the transducer assembly 512, wherein the transducer assembly 512 is insertable into the housing 522 through the opening 524. In one variation, the transducer assembly 512 includes a stacked plurality 526 of piezoelectric transducer disks 528. In a first example, the first transducer-assembly-to-housing mounting feature 518 is a first outward flange of the transducer assembly 512, and the second transducer-assembly-to-housing mounting feature 520 is second outward flange of the transducer assembly 512, wherein the first outward flange projects more (or less) than the second outward flange.

Figure 22:
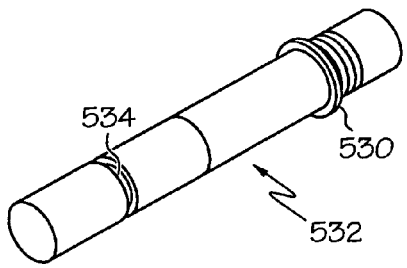
FIGS. 22 through 25 are side elevational schematic views of alternate embodiments of the transducer assembly of the handpiece of FIG. 21.

In a second example, as shown in the alternate embodiment of FIG. 22, the first transducer-assembly-to-housing mounting feature 530 is an outward flange of the transducer assembly 532, and the second transducer-assembly-to-housing mounting feature 534 is an O-ring groove of the transducer assembly 532. The outward flange projects more (or less) than an O-ring (not shown) disposed in the O-ring groove.

Figure 23:
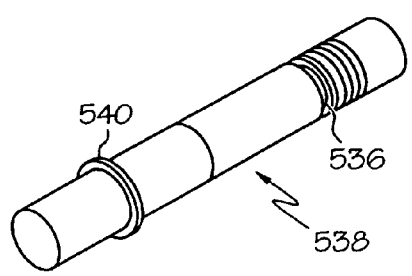

In a third example, as shown in the alternate embodiment of FIG. 23, the first transducer-assembly-to-housing mounting feature 536 is an O-ring groove of the transducer assembly 538, and the second transducer-assembly-to-housing mounting feature 540 is an outward flange of the transducer assembly 538. An O-ring (not shown) disposed in the O-ring groove projects more (or less) than the outward flange.

Figure 24:
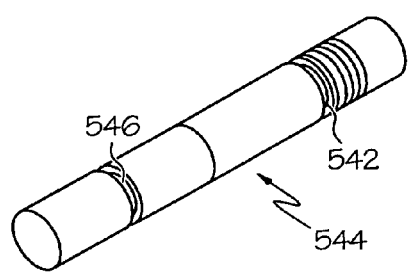

In a fourth example, as shown in the alternate embodiment of FIG. 24, the first transducer-assembly-to-housing mounting feature 542 is a first O-ring groove of the transducer assembly 544, and the second transducer-assembly-to-housing mounting feature 546 is second O-ring groove of the transducer assembly 544. A first O-ring (not shown) disposed in the first O-ring groove projects more (or less) than a second O-ring (not shown) disposed in the second O-ring groove.

Figure 25:
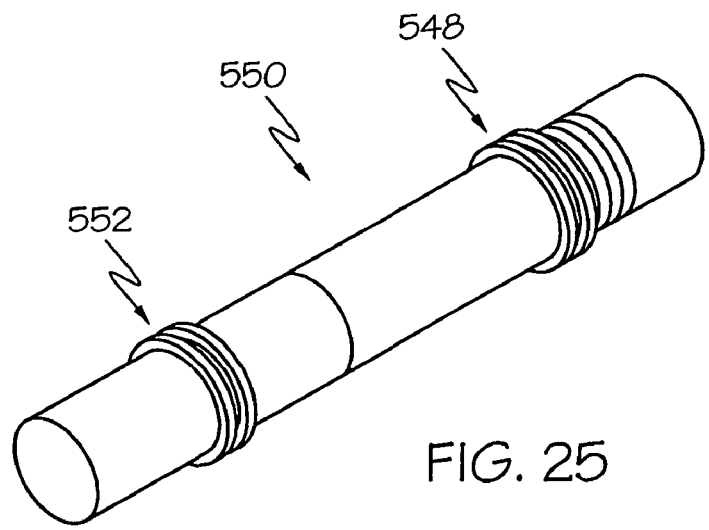
Figure 26:
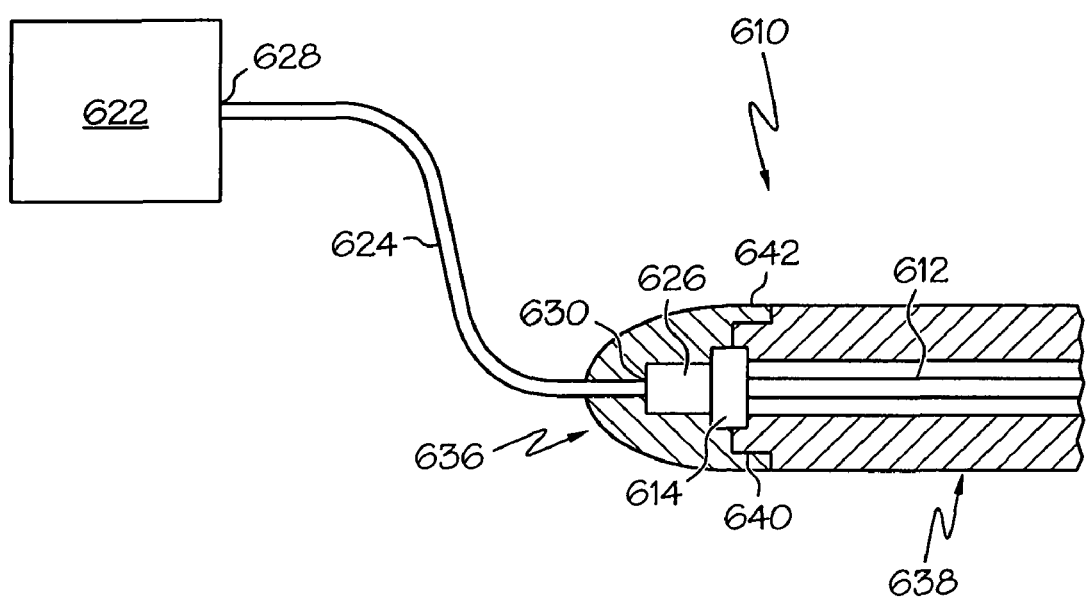
FIG. 26 is a side elevational schematic view of an eighth embodiment of the invention showing a medical ultrasound handpiece connected to an ultrasound electric generator with the end cap and the housing of the handpiece shown in cutaway.

In a fifth example, as shown in the alternate embodiment of FIG. 25, the first transducer-assembly-to-housing mounting feature 548 is a first pair of O-ring-bounding outward flanges of the transducer assembly 550, and the second transducer-assembly-to-housing mounting feature 552 is a second pair of O-ring-bounding outward flanges of the transducer assembly 550. A first O-ring (not shown) bounded by the first pair of O-ring-bounding outward flanges projects more (or less) than a second O-ring (not shown) bounded by the second pair of O-ring-bounding outward flanges.

An eighth embodiment of the invention is shown in FIGS. 26-29. A first expression of the embodiment of FIGS. 26-29 is for a medical ultrasound handpiece 610 including a medical ultrasound transducer assembly 612 and an annular connector assembly 614 (which is also called an annular bumper assembly). The transducer assembly 612 includes a metallic end-mass component 616, a piezoelectric transducer disk 618, and an electrode 620. The piezoelectric transducer disk 618 is located distal the end-mass component 616 and is in electrical contact with the electrode 620. The connector assembly 614 surrounds the transducer assembly 612, is in electrical contact (such as at least in part by wiring 623) with the electrode 620, and is electrically connectable to an ultrasound electric generator 622.

In one enablement of the first expression of the embodiment of FIGS. 26-29, the medical ultrasound handpiece 610 includes an electric cable 624 and a cable socket 626, wherein the cable 624 has a proximal end 628 electrically connectable to the ultrasound electric generator 622 and has a distal end 630 electrically connected to the cable socket 626, and wherein the end-mass component 616 is disposable within the cable socket 626. In one variation, the cable socket 626 has connector pins 632, and the connector assembly 614 has connector pins 634 which are engagable with the connector pins 632 of the cable socket 626. In one modification, the handpiece 610 includes an end cap 636, wherein the cable socket 626 is disposable in the end cap 636. In one example, the handpiece 610 includes a housing 638, wherein the housing 638 surrounds the connector assembly 614 and has a proximal end portion 640, and wherein the end cap 636 has a distal end portion 642 which is press-fittingly attachable to the proximal end portion 640 of the housing 638.

A second expression of the embodiment of FIGS. 26-29 is for a medical ultrasound handpiece 610 including a medical ultrasound transducer assembly 612 and an annular connector assembly 614. The transducer assembly 612 includes a metallic end-mass component 616, a stacked plurality 644 of piezoelectric transducer disks 618, and electrodes 620. The stacked plurality 644 of piezoelectric transducer disks 618 is located distal the end-mass component 616. Each piezoelectric transducer disk 618 is in electrical contact with a corresponding electrode 620. The connector assembly 614 surrounds the transducer assembly 612, is in electrical contact (such as at least in part by wiring 623) with the electrodes 620, and is electrically connected to a cable socket 626 which is electrically connectable to an ultrasound electric generator 622.

Figure 27:
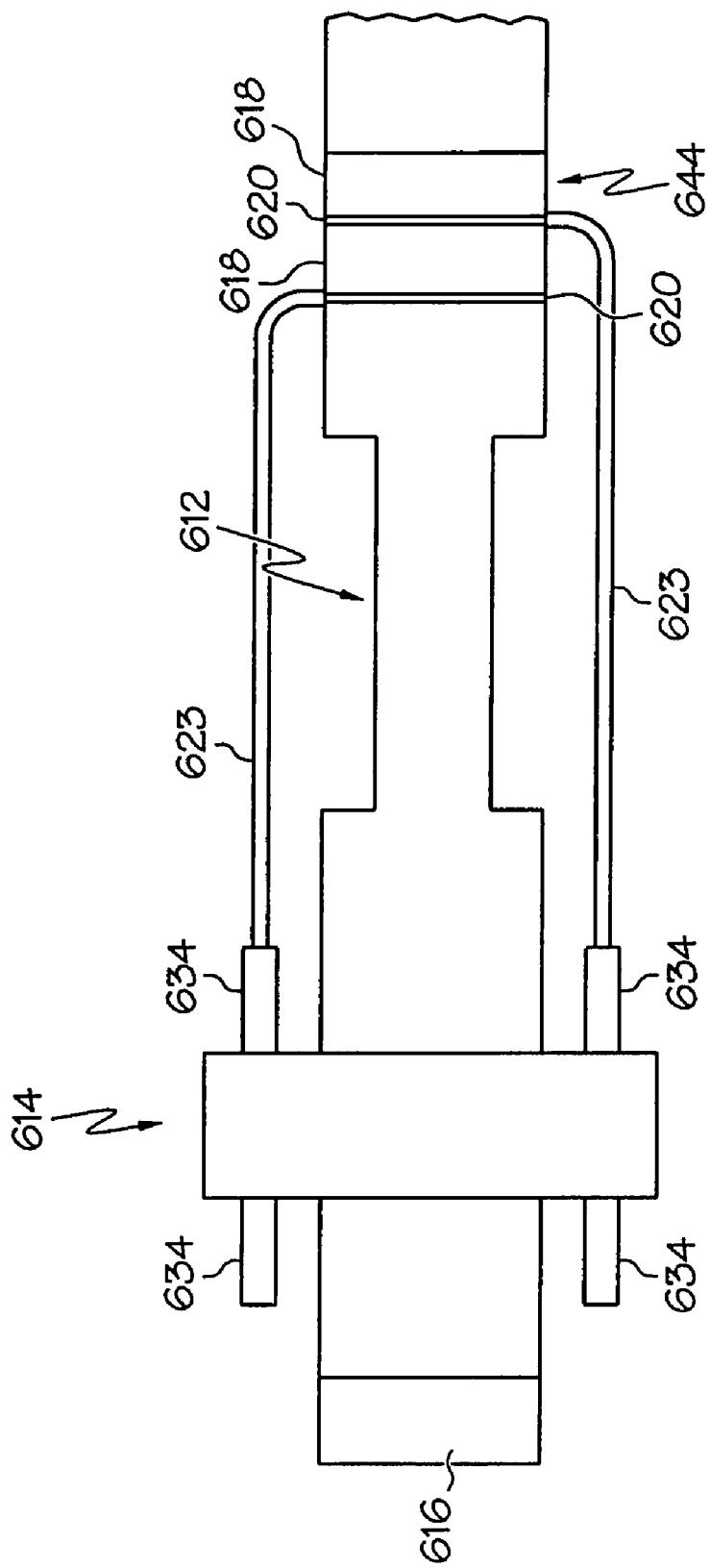
FIG. 27 is an enlarged side elevational view of the annular connector assembly and a portion of the medical ultrasound transducer assembly of the handpiece of FIG. 26.
Figure 28:
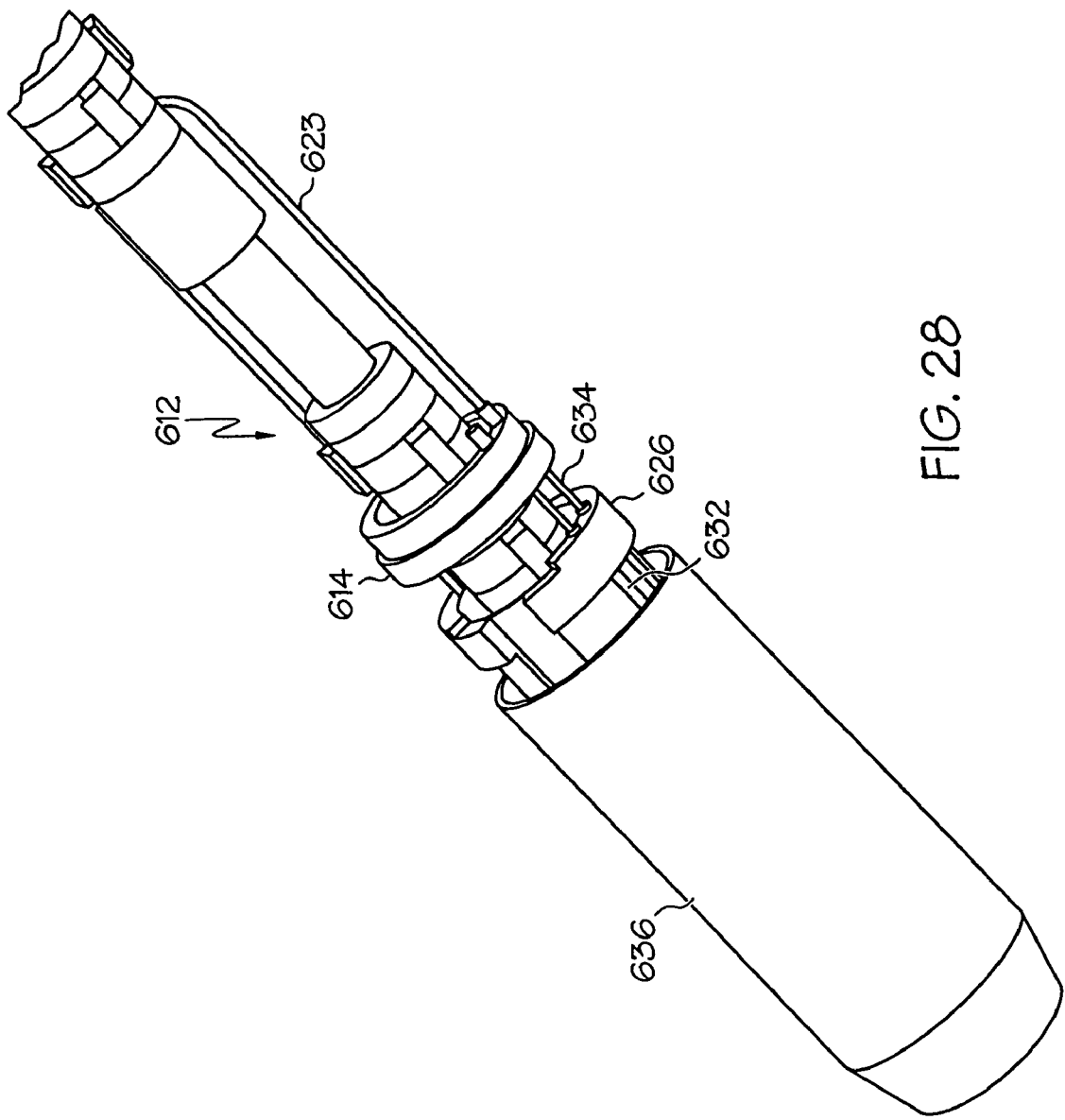
FIG. 28 is a perspective view of the end cap, the cable socket, the annular connector assembly, and the medical ultrasound transducer assembly of the handpiece of FIG. 26.
Figure 29:
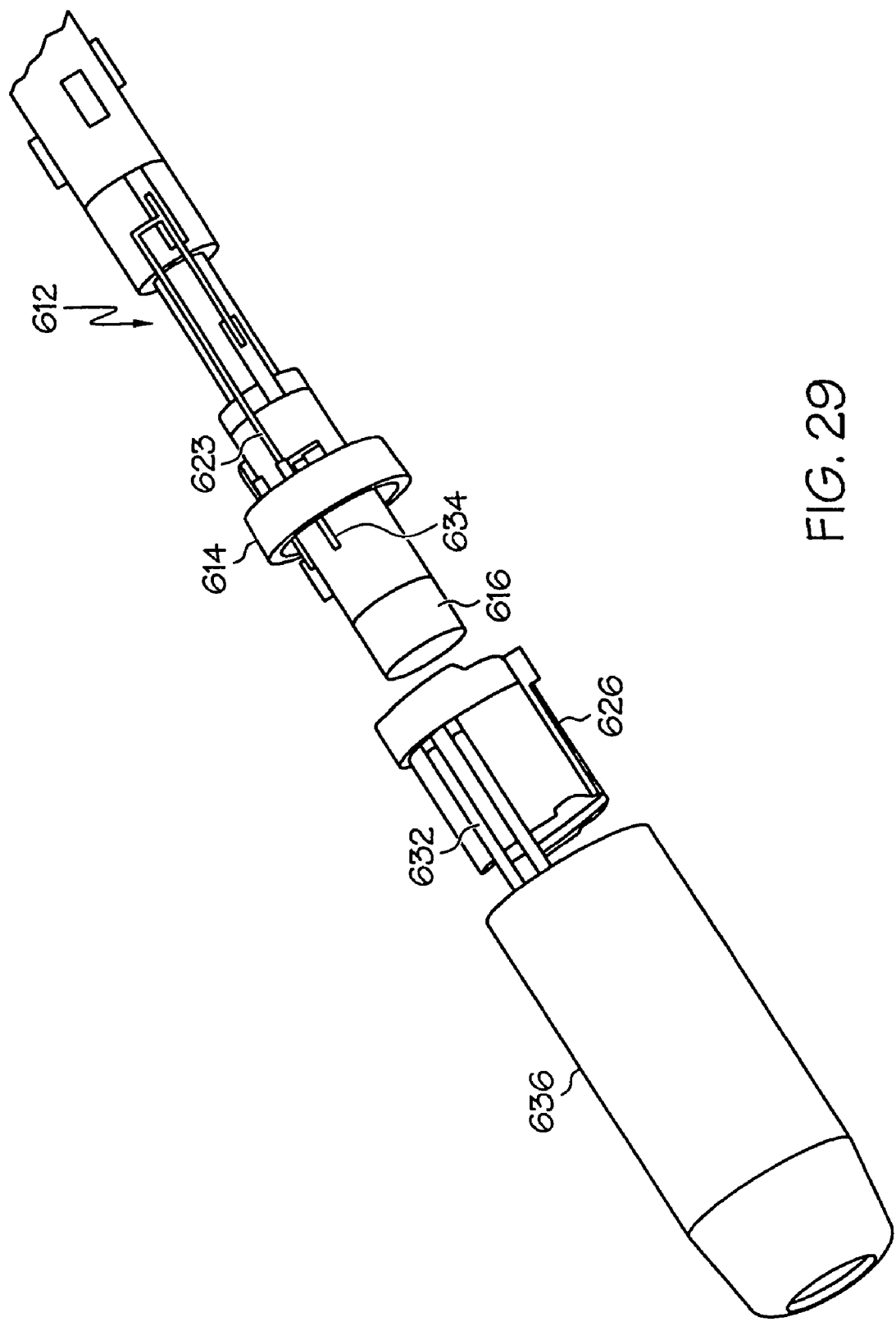
FIG. 29 is an exploded view of the assemblage of FIG. 28.

It is noted that in FIG. 27, the left-most of the two shown piezoelectric transducer disks 618 is in electrical contact with the left-most (but not the right-most) of the two shown electrodes 620 and the right-most of the two shown piezoelectric transducer disks 618 is in electrical contact with the right-most (but not the left-most) of the two shown electrodes 620.

In one enablement of the second expression of the embodiment of FIGS. 26-29, the medical ultrasound handpiece 610 includes an electric cable 624, wherein the cable 624 has a proximal end 628 electrically connectable to the generator 622 and has a distal end 630 electrically connected to the cable socket 626, and wherein the end-mass component 616 is disposed within the cable socket 626. In one variation, the cable socket 626 has connector pins 632, and the connector assembly 614 has connector pins 634 which are engaged with the connector pins 632 of the cable socket 626. In one modification, the handpiece 610 includes an end cap 636, wherein the cable socket 626 is disposed in the end cap 636. In one example, the handpiece 610 includes a housing 638, wherein the housing 638 surrounds the connector assembly 614 and has a proximal end portion 640, and wherein the end cap 636 has a distal end portion 642 which is press-fittingly attached to the proximal end portion 640 of the housing 638.

A ninth embodiment of the invention is shown in FIGS. 30-32. A first expression of the embodiment of FIGS. 30-32 is for a medical ultrasound handpiece 710 including a medical ultrasound transducer assembly 712, an inner conductive ring 714, and an outer conductive ring 716. The transducer assembly 712 is electrically connectable to an ultrasound electric generator 718, has a longitudinal axis 720, and is attachable to an ultrasonically-vibratable medical-treatment instrument 722 having a switch 744 which has an open position and a closed position. The inner conductive ring 714 is substantially coaxially aligned with the longitudinal axis 720, surrounds the transducer assembly 712, and has a distally-facing first annular surface 746. The outer conductive ring 716 is substantially coaxially aligned with the longitudinal axis 720, surrounds the transducer assembly 712, and has a distally-facing second annular surface 748. The outer conductive ring 716 is electrically isolated from the inner conductive ring 714. The first and second annular surfaces 746 and 748 are in electric contact with the switch 744 of the attached instrument 722 when the switch 744 is in the closed position. The inner and outer conductive rings 714 and 716 are electrically connectable to the generator 718, and the switch 744 of the attached instrument 722 controls the connected generator 718.

In one enablement of the first expression of the embodiment of FIGS. 30-32, the transducer assembly 712 is attached to the instrument 722. In one variation, the transducer assembly 712 distally terminates in a stud 750 which is attachable to the instrument 722. In one modification, the stud 750 is threadably attachable to the instrument 722.

In one implementation of the first expression of the embodiment of FIGS. 30-32, the handpiece 710 includes an annular dielectric member 758, wherein the inner and outer conductive rings 714 and 716 are separated by the dielectric member 758. In one the inner and outer conductive rings 714 and 716 are electrically connected to the generator 718. In one variation, an electric cable 752 extends from the handpiece 710 to a proximal plug 754 which is attachable to the generator 718, and wiring 756 extends from the cable 752 within the handpiece 710 to the transducer assembly 712, to the inner conductive ring 714, and to the outer conductive ring 716. In an alternate variation, not shown, wiring does not extend directly from the cable to the outer conductive ring but extends to the housing which electrically contacts the outer conductive ring, wherein the housing serves as electrical ground. In one example, the transducer assembly 712 is attached to the instrument 722.

In one construction of the first expression of the embodiment of FIGS. 30-32, closing the switch 744 causes a first switch pin 760 to electrically contact the inner conductive ring 714 and causes a second switch pin 762 to electrically contact the outer conductive ring 716. In the same or a different construction, the handpiece 710 includes a housing 764 and a nose cone assembly 766, wherein the nose cone assembly 766 is attached to the housing 764 and includes the inner conductive ring 714, the outer conductive ring 716, and the dielectric member 758. In one modification, mounts 768 disposed at nodes of the transducer assembly 712 secure the transducer assembly 712 within and to the housing 764, wherein the mounts 768 have openings to pass the wiring 756 from the cable 752 to the inner and outer conductive rings 714 and 716.

In one application of the first expression of the embodiment of FIGS. 30-32, the instrument 722 has an ultrasonically vibratable portion 770 which is attachable to the stud 750 and has a surrounding non-vibratable portion 772. The non-vibratable portion 772 surrounds the vibratable portion 770 and includes the switch 744. In one variation, the switch 744 is a two button switch (such as that described in US Patent Application Publications 2004/0147947 and 2002/0057541). In another variation, not shown, the switch is a one button switch. Other designs of the switch and modes of generator control by the switch, are left to those skilled in the art.

Figure 33:
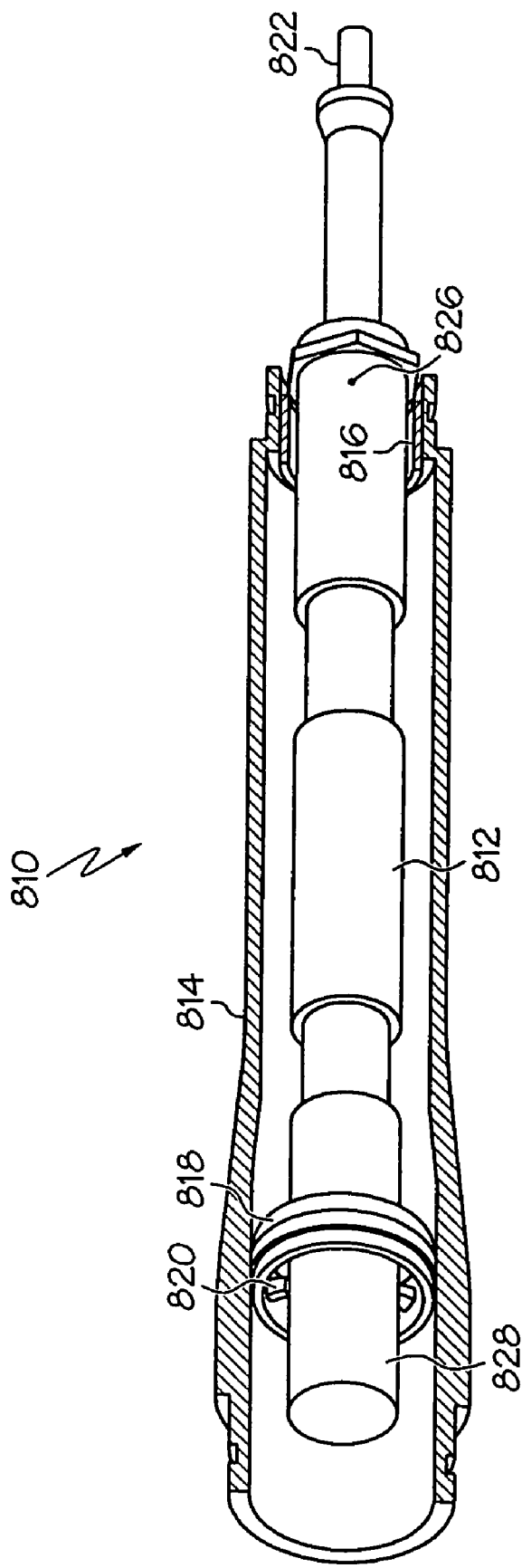
FIG. 33 is a perspective view of a tenth embodiment of the invention showing a medical ultrasound handpiece including a housing (shown in cutaway), a medical ultrasound transducer assembly, a mount (shown in cutaway) pivotally attaching the transducer assembly to the housing, and a bumper unit attached to the housing.
Figure 35:
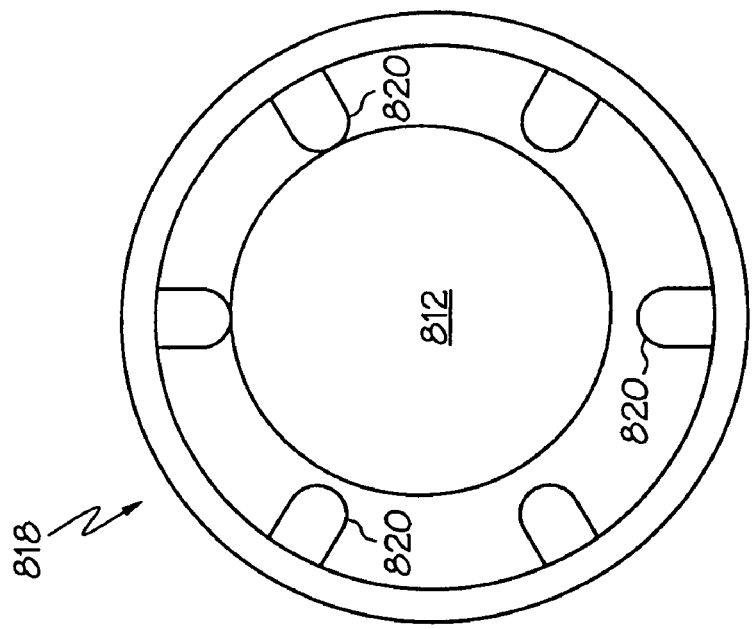
FIG. 35 is a proximal end view of the transducer assembly and the bumper unit of FIG. 33 when the mount is under a pivoting load.
Figure 34:
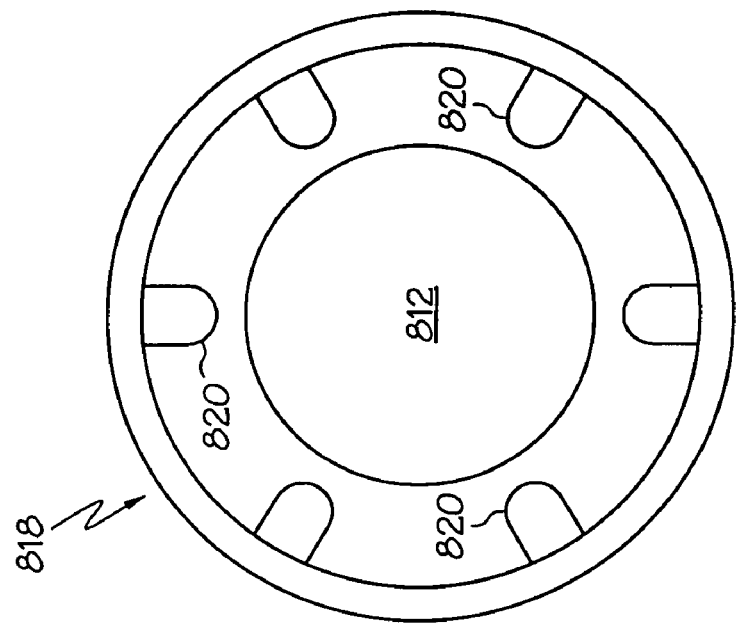
FIG. 34 is a proximal end view of the transducer assembly and the bumper unit of FIG. 33 when the mount is not under a pivoting load.

A tenth embodiment of the invention is shown in FIGS. 33-35. A first expression of the embodiment of FIGS. 33-35 is for a medical ultrasound handpiece 810 including a medical ultrasound transducer assembly 812, a housing 814, a mount 816, and an annular bumper unit 818. The housing 814 surrounds the transducer assembly 812. The mount 816 pivotally attaches the transducer assembly 812 to the housing 814. The bumper unit 818 is attached to the housing 814 and includes a plurality of spaced apart and inwardly projecting bumpers 820. None of the bumpers 820 is in contact with the transducer assembly 812 when the transducer assembly 812 is not under a pivoting load (as shown in FIG. 34). At least one of the bumpers 820 is contact with the transducer assembly 812 when the transducer assembly 812 is under the pivoting load (as shown in FIG. 35).

A pivoting load is a load which causes the transducer assembly 812 to pivot about the mount 816 with respect to the housing 814. In one application, the transducer assembly 812 distally terminates in a stud 822, and an ultrasonically-vibratable medical-treatment instrument (not shown) is attachable to the stud 822. In one example, a pivoting load is produced when a surgeon holds the housing 814 and presses down on patient tissue with the distal end of the attached instrument which causes the transducer assembly 812 to pivot about the mount 816 with respect to the housing 814 and causes the transducer assembly 812 proximal the mount 816 to contact at least one of the bumpers 820 as shown in FIG. 35. It is noted that a small area of contact of the transducer assembly 812 with the bumpers 820 should reduce damping and power loss.

In one construction of the first expression of the embodiment of FIGS. 33-35, the mount 816 includes an elastomeric ring. Other constructions and types of mounts are left to the artisan.

In one enablement of the first expression of the embodiment of FIGS. 33-35, the transducer assembly 812 has a distal-most node 826, and the mount 816 is in contact with the transducer assembly 812 proximate the distal-most node 826. In one variation, the transducer assembly 812 has a proximal-most node 828, and the bumper unit 818 is disposed proximate the proximal-most node 828. In one example, the bumper unit 818 is press-fittingly attached to the housing 814. In one illustration, the transducer assembly 812 is a 1½-wave transducer assembly.

An eleventh embodiment of the invention is shown in FIGS. 36-42. A first expression of the embodiment of FIGS. 36-42 is for a medical ultrasound handpiece 910 including a medical ultrasound transducer assembly 912, at least one mounting member 914, and a first housing component 916. The transducer assembly 912 has a longitudinal axis 918 and has a substantially coaxially aligned, circumferential surface groove 920. The at-least-one mounting member 914 is at-least-partially-annular and has an inner portion 922 located in the surface groove 920. The first housing component 916 surrounds the transducer assembly 912 and has a distal end portion 924 including an annular longitudinally-facing surface 926 with a recessed seat 928. The at-least-one mounting member 914 has at least a proximal portion 930 located in the seat 928.

In a first construction of the first expression of the embodiment of FIGS. 36-42, the at-least-one mounting member 914 is a partially annular monolithic mounting member. In a second construction, not shown, the at-least-one mounting member includes a plurality (such as two) mounting members disposed in a partially annular array. In one choice of materials, the at-least-one mounting member 914 is dielectric (or at least the inner portion 922 is dielectric or coated with a dielectric material) to electrically isolate the distal end portion 924 of the first housing component 916 from the surface groove 920 of the transducer assembly 912. In one example, the at-least-one mounting member 914 is elastomeric. In one employment, the gap, when the at-least-one mounting member 914 has a partially-annular construction, allows for the passage of wiring (not shown). Other constructions, including fully annular constructions, are left to the artisan.

In one enablement of the first expression of the embodiment of FIGS. 36-42, the handpiece 910 includes a second housing component 932 surrounding the transducer assembly 912 and having a proximal end portion 934 which surrounds and is attached to the distal end portion 924 of the first housing component 916. In one variation, the proximal end portion 934 of the second housing component 932 includes an internal annular ledge 936 which seats against a distal portion 938 of the at-least-one mounting member 914. In one variation, the proximal end portion 934 of the second housing component 932 is press-fittingly attached to the distal end portion 924 of the first housing component 916. In one example, the transducer assembly 912 has a distal-most node 940, and the surface groove 920 is disposed proximate the distal-most node 940.

In one employment of the first expression of the embodiment of FIGS. 36-42, the first housing component 916 is referred to as the housing and the second housing component 932 is referred to as the nose cone. It is noted that in schematic FIG. 37, the transducer assembly 912 is shown with jumpers 942, wherein jumpers have been discussed in one or more previous embodiments.

In a first method of assembly of the handpiece 910, the proximal end (the left end in FIG. 37) of the transducer assembly 912 is not conventionally inserted into the distal end opening (the right end opening in FIG. 37) of the first housing component 916 wherein the protruding jumpers 942 and wiring (not shown) at the stacked plurality or (stacked pluralities) of piezoelectric transducer disks (not shown) of the transducer assembly 912 have to be fished through the narrow distal end opening. Rather, by making the at-least-one mounting member 914 be a separate piece (or separate pieces) from the transducer assembly 912 and act as a conventional transducer assembly mounting flange, the distal end (the right end in FIG. 37) of the transducer assembly 912 is inserted in the proximal end opening (the left end opening in FIG. 37) of the first housing component 916, and pushed to the position shown in FIG. 38 exposing the surface groove 920 of the transducer assembly 912 beyond the distal end (the right end in FIG. 38) of the first housing component 916.

Figure 36:
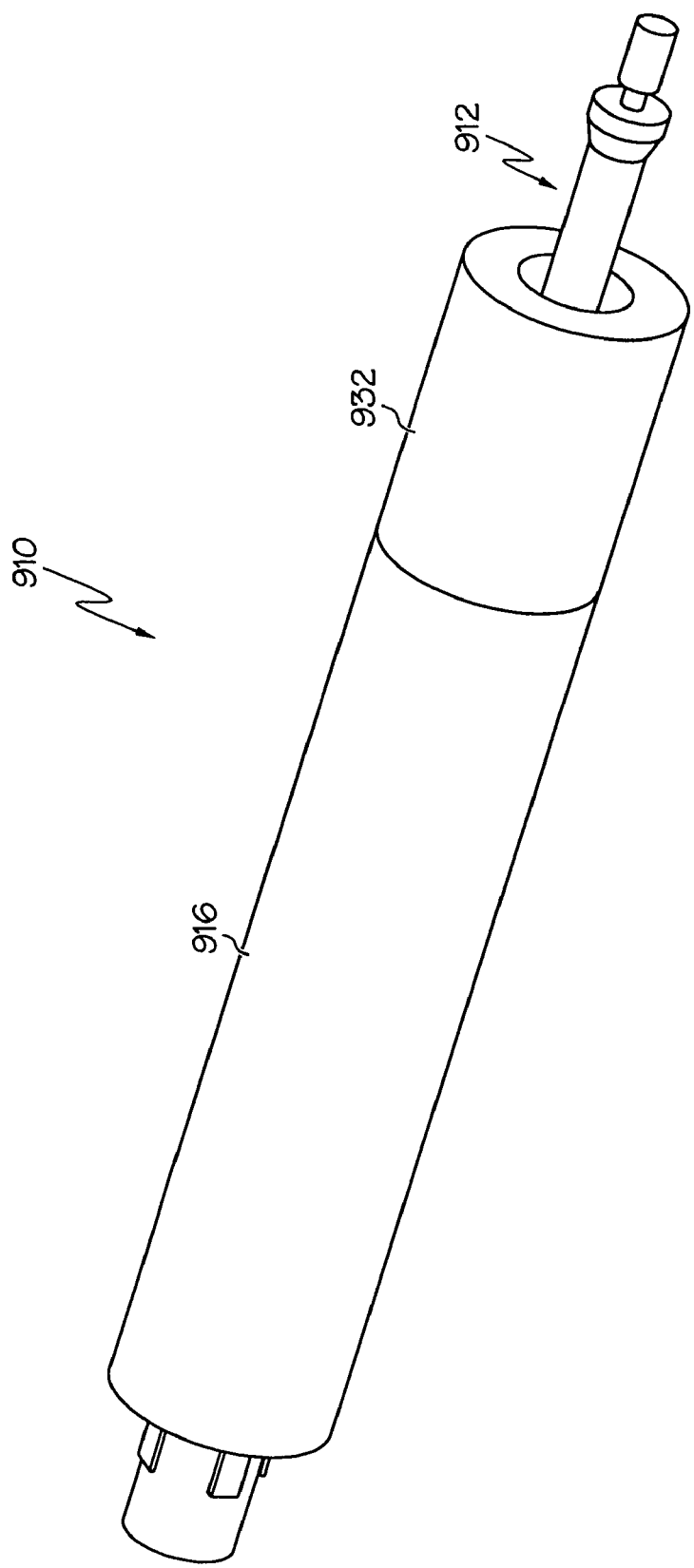
FIG. 36 is a perspective view of an eleventh embodiment of the invention showing a medical ultrasound handpiece.
Figure 37:
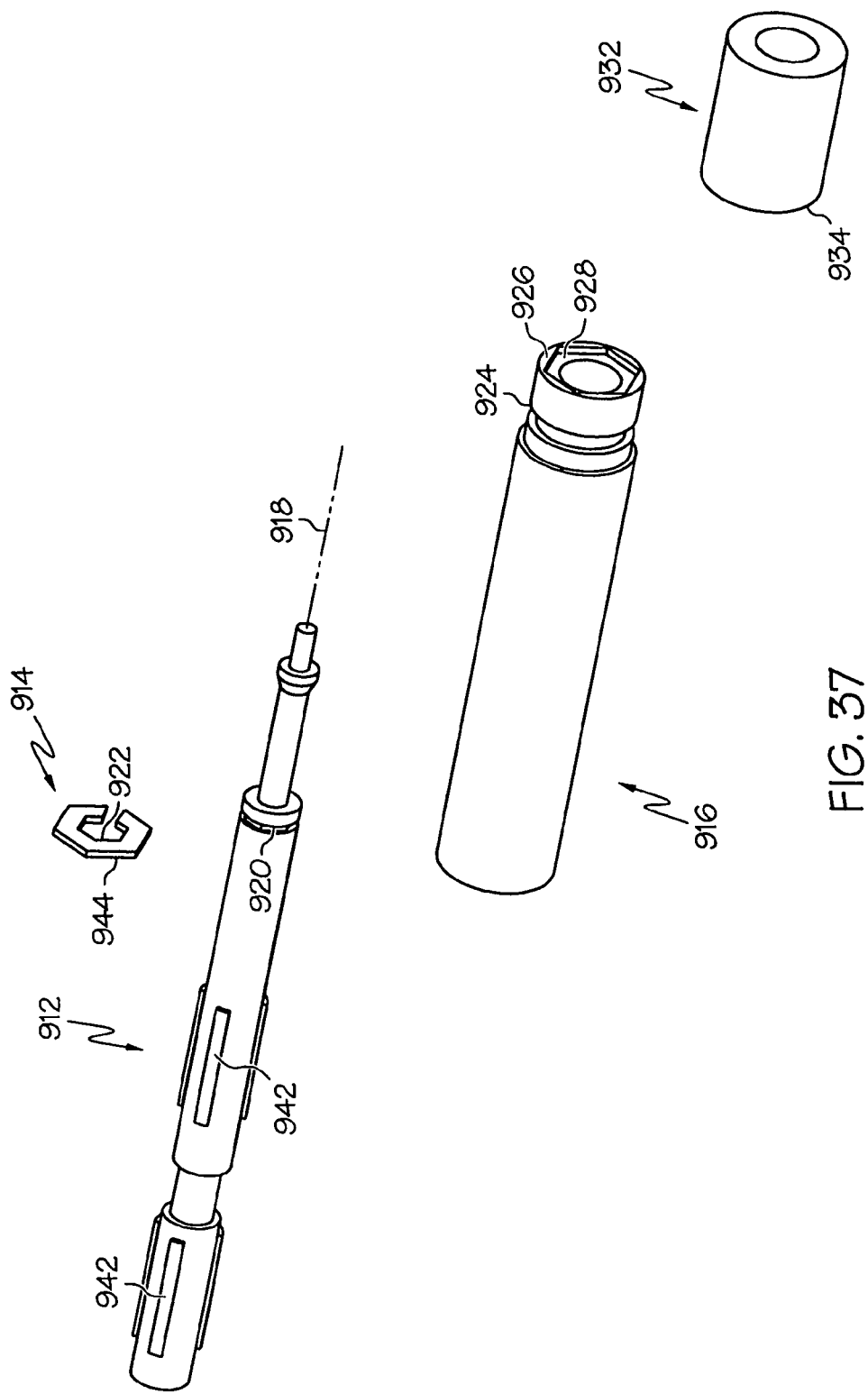
FIG. 37 is an exploded view of the handpiece of FIG. 36 showing the medical ultrasound transducer assembly (which is schematically illustrated), the at-least-one mounting member, the first housing component, and the second housing component of the handpiece of FIG. 36.
Figure 38:
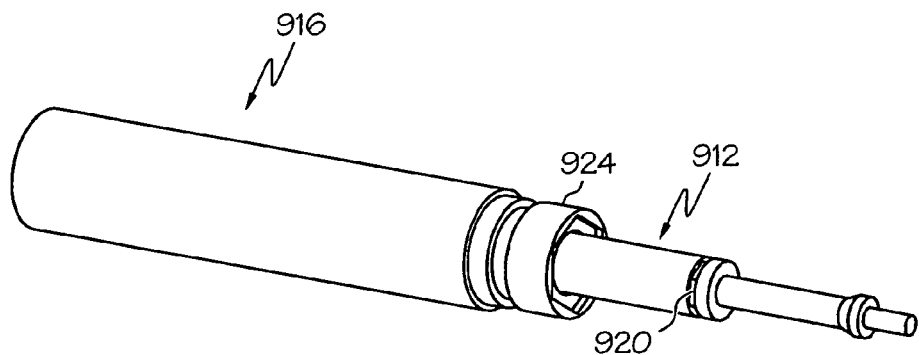
FIGS. 38-40 are perspective views showing intermediate stages of assembling the components of FIG. 37 to produce the assembled handpiece of FIG. 36.
Figure 39:
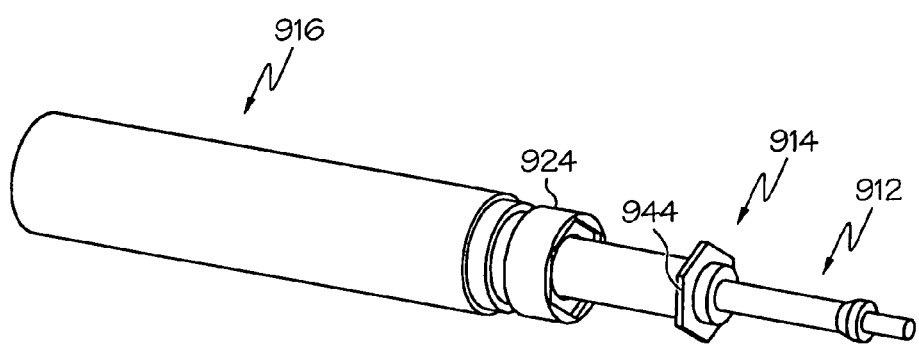
Figure 40:
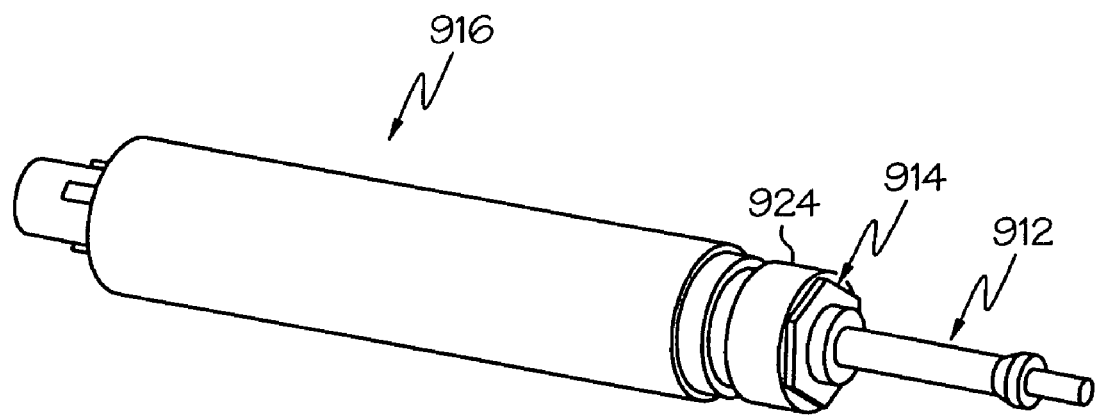
Figure 42:
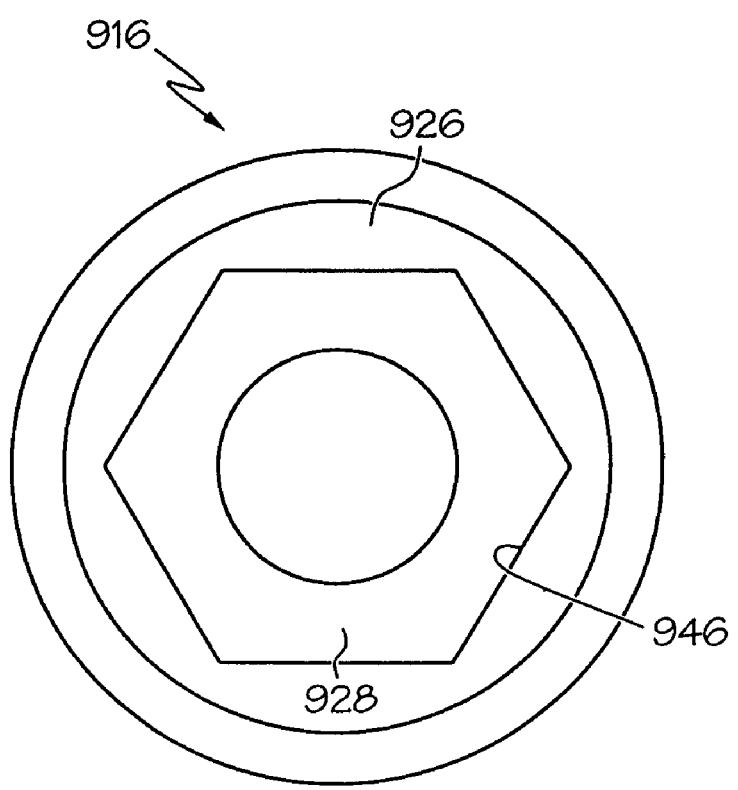
FIG. 42 is a distal end view of the first housing component of FIG. 37.
Figure 41:
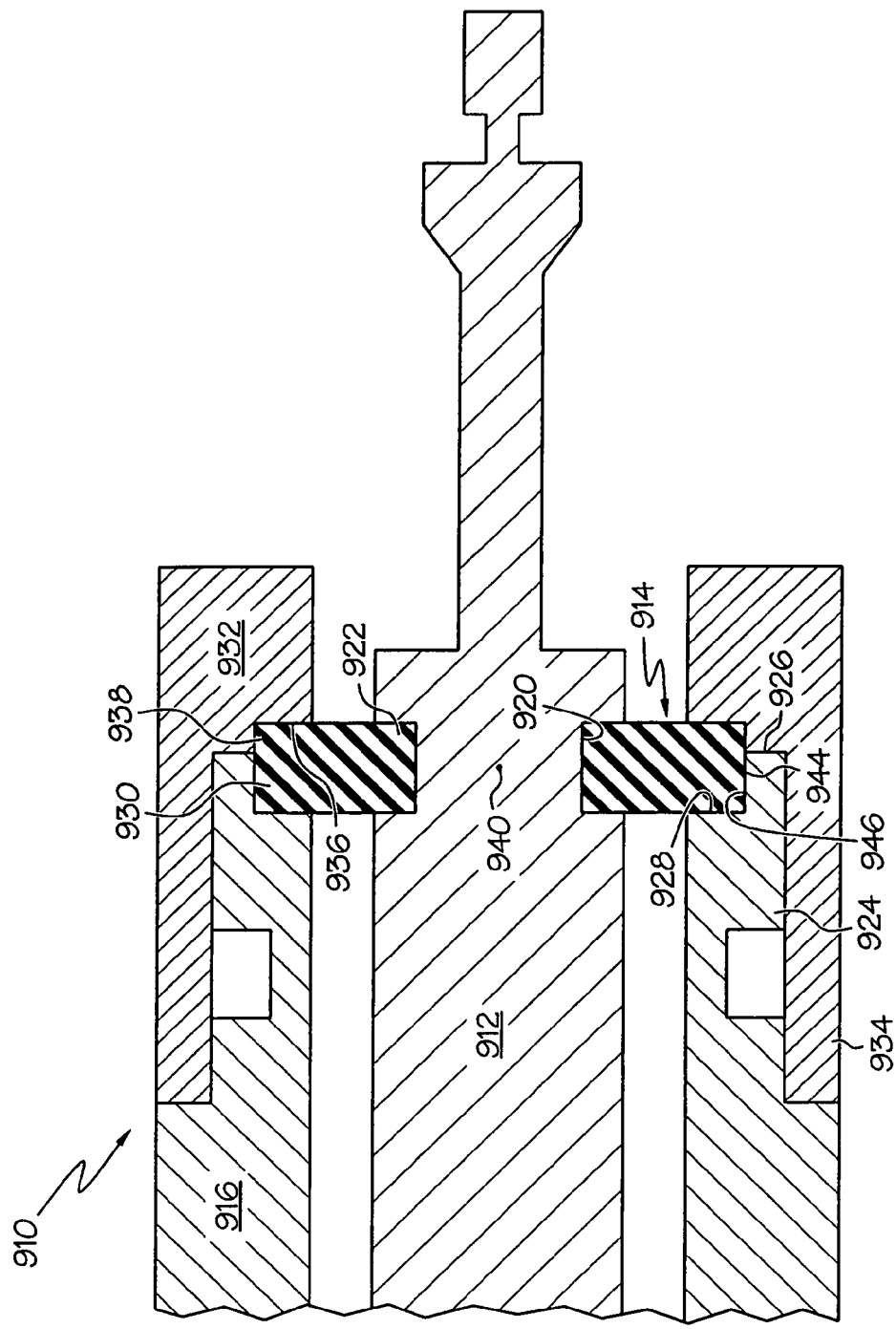
FIG. 41 is a cross sectional view of a distal portion of the handpiece of FIG. 36.

Continuing with the assembly, then the at least-one-mounting member 914 is installed in the surface groove 920 as shown in FIG. 39. Then, the transducer assembly 912 is moved proximally within the first housing component 916 to seat the proximal portion 930 of the at least-one-mounting member 914 within the recessed seat 928 of the longitudinally-facing surface 926 of the distal end portion 924 of the first housing component 916 as shown in FIG. 40. Then, the proximal end portion 934 of the second housing component 932 is press fittingly attached to the distal end portion 924 of the first housing component 916 as shown in FIG. 36.

In one arrangement of the first expression of the embodiment of FIGS. 36-42, the at-least-one mounting member 914 has at least one peripheral flat 944 which engages a corresponding at least one peripheral flat 946 on the recessed seat 928 of the longitudinally-facing surface 926 of the distal end portion 924 of the first housing component 916. This prevents rotation of the at-least-one mounting member 914. In the same or a different arrangement, the at-least-one mounting member 914 is flexible (i.e., can be flexed by an adult person of average strength) to facilitate installation.

Several benefits and advantages are obtained from one or more of the expressions of embodiments of the invention. In one example, one or more or all of the expressions of embodiments of the invention help enable a relatively small size medical ultrasound transducer assembly to provide an attached ultrasonically-vibratable medical-treatment instrument with a desirable high displacement (i.e., a large vibrational amplitude) resulting in a relatively small size handpiece which is suitable for a surgeon to hold and use in precise and delicate surgery.

While the present invention has been illustrated by a description of several expressions, embodiments, and examples, etc. thereof, it is not the intention of the applicants to restrict or limit the spirit and scope of the appended claims to such detail. Numerous other variations, changes, and substitutions will occur to those skilled in the art without departing from the scope of the invention. It will be understood that the foregoing description is provided by way of example, and that other modifications may occur to those skilled in the art without departing from the scope and spirit of the appended Claims.

What is claimed is:

1. A medical ultrasound handpiece comprising:
 a) a medical ultrasound transducer assembly;
 b) a housing surrounding the transducer assembly;
 c) a mount pivotally attaching the transducer assembly to the housing; and
 d) an annular bumper unit attached to the housing and including a plurality of spaced apart and inwardly projecting bumpers, wherein none of the bumpers is in contact with the transducer assembly when the transducer assembly is not under a pivoting load, and wherein at least one of the bumpers is in contact with the transducer assembly when the transducer assembly is under the pivoting load.

2. The medical ultrasound handpiece of claim 1, wherein the transducer assembly has a distal-most node, and wherein the mount is in contact with the transducer assembly proximate the distal-most node.

3. The medical ultrasound handpiece of claim 2, wherein the transducer assembly has a proximal-most node, and wherein the bumper unit is disposed proximate the proximal-most node.

4. The medical ultrasound handpiece of claim 3, wherein the bumper unit is press-fittingly attached to the housing.

5. The medical ultrasound handpiece of claim 4, wherein the transducer assembly is a 1½-wave transducer assembly.

6. The medical ultrasound handpiece of claim 1, wherein the transducer assembly has a proximal-most node, and wherein the bumper unit is disposed proximate the proximal-most node.

7. The medical ultrasound handpiece of claim 6, wherein the bumper unit is press-fittingly attached to the housing.

8. The medical ultrasound handpiece of claim 7, wherein the transducer assembly is a 1½-wave transducer assembly.

9. The medical ultrasound handpiece of claim 1, wherein the bumper unit is press-fittingly attached to the housing.

10. The medical ultrasound handpiece of claim 9, wherein the transducer assembly is a 1½-wave transducer assembly.

11. The medical ultrasound handpiece of claim 1, wherein the transducer assembly is a 1½-wave transducer assembly.

12. The medical ultrasound handpiece of claim 1, wherein the transducer assembly terminates in a stud, and wherein an ultrasonically-vibratable medical-instrument is attachable to the stud.

13. The medical ultrasound handpiece of claim 1, wherein the mount includes an elastomeric ring.

14. A medical ultrasound handpiece comprising:
 a) a medical ultrasound transducer assembly having a longitudinal axis;
 b) a housing surrounding the transducer assembly and having a longitudinal axis;
 c) a distal mount pivotally attaching the transducer assembly to the housing, wherein the mount is configured to allow the transducer assembly to pivot about the mount with respect to the housing, such that the longitudinal axis of the transducer assembly is obliquely angled with respect to the longitudinal axis of the housing, when the transducer assembly is under a pivoting load; and
 d) a proximal annular bumper unit attached to the housing surrounding the transducer assembly and including a plurality of spaced apart and inwardly projecting bumpers, wherein none of the bumpers is in contact with the transducer assembly when the transducer assembly is not under the pivoting load, and wherein at least one of the bumpers is in contact with the transducer assembly when the transducer assembly is under the pivoting load.

15. The medical ultrasound handpiece of claim 14, wherein the transducer assembly has a distal-most node, and wherein the mount pivotally attaches the transducer assembly to the housing proximate the distal-most node.

16. The medical ultrasound handpiece of claim 15, wherein the transducer assembly terminates in a stud projecting distally beyond the housing, and wherein an ultrasonically-vibratable medical-instrument is attachable to the stud.

17. The medical ultrasound handpiece of claim 14, wherein the transducer assembly has a proximal-most node, and wherein the bumper unit is disposed proximate the proximal-most node.

18. The medical ultrasound handpiece of claim 17, wherein the bumper unit is press-fittingly attached to the housing.

19. The medical ultrasound handpiece of claim 14, wherein the transducer assembly is a 1½-wave transducer assembly.

\* \* \* \* \*